(12) United States Patent
Harding et al.

(10) Patent No.: US 11,452,618 B2
(45) Date of Patent: Sep. 27, 2022

(54) SPINAL ARTIFICIAL DISC REMOVAL TOOL

(71) Applicant: DIMICRON, INC, Orem, UT (US)

(72) Inventors: David Harding, Provo, UT (US); Jeffery Karl Taylor, Loomis, CA (US); Eric Lange, Draper, UT (US)

(73) Assignee: DIMICRON, INC, Orem, UT (US)

( * ) Notice: Subject to any disclaimer, the term of this patent is extended or adjusted under 35 U.S.C. 154(b) by 0 days.

(21) Appl. No.: 17/028,888

(22) Filed: Sep. 22, 2020

(65) Prior Publication Data

US 2021/0085487 A1  Mar. 25, 2021

Related U.S. Application Data

(60) Provisional application No. 62/904,680, filed on Sep. 23, 2019.

(51) Int. Cl.
*A61F 2/46* (2006.01)

(52) U.S. Cl.
CPC ..... *A61F 2/4611* (2013.01); *A61F 2002/4619* (2013.01)

(58) Field of Classification Search
CPC .......................... A61F 2/4611; A61F 2002/4619
See application file for complete search history.

(56) References Cited

U.S. PATENT DOCUMENTS

| 2,721,492 | A | * | 10/1955 | Prevost | H01K 3/32 |
| | | | | | 81/445 |
| 3,574,381 | A | * | 4/1971 | Ocheltree | B25B 9/00 |
| | | | | | 294/94 |
| 3,819,814 | A | | 6/1974 | Pope | |
| 3,864,409 | A | | 2/1975 | Pope | |
| 4,055,862 | A | | 11/1977 | Farling | |
| 4,104,344 | A | | 8/1978 | Pope et al. | |
| 4,163,769 | A | | 8/1979 | Pope et al. | |
| 4,164,794 | A | | 8/1979 | Spector et al. | |
| 4,166,292 | A | | 9/1979 | Bokros | |
| 4,196,181 | A | | 4/1980 | Vereschasin et al. | |
| 4,289,123 | A | | 9/1981 | Dunn | |
| 4,714,469 | A | | 12/1987 | Kenna | |
| 4,759,766 | A | | 7/1988 | Buettner-Janz et al. | |
| 4,759,769 | A | | 7/1988 | Hedman et al. | |
| 5,258,031 | A | | 11/1993 | Salib et al. | |
| 5,401,269 | A | | 3/1995 | Büttner-Janz et al. | |

(Continued)

FOREIGN PATENT DOCUMENTS

JP  01-308557  12/1989
JP  10-501705  2/1998

(Continued)

OTHER PUBLICATIONS

WIPO, ISR and Written Opinion from PCT/US2020/052072.
Depuy Synthes, Prodisc-C Vivo surgical technique, 2015.

*Primary Examiner* — Kevin T Truong
*Assistant Examiner* — Diana Jones
(74) *Attorney, Agent, or Firm* — Brett Peterson; Pate Peterson PLLC

(57) ABSTRACT

An extraction tool for removing an installed artificial disc from a spine is provided. The extraction tool is impacted between the artificial disc and the vertebrae and engages the artificial disc to allow a surgeon to remove the artificial disc from the spine.

30 Claims, 11 Drawing Sheets

(56) References Cited

U.S. PATENT DOCUMENTS

| | | |
|---|---|---|
| 5,425,773 A | 6/1995 | Boyd et al. |
| 5,496,318 A | 3/1996 | Howland et al. |
| 5,534,029 A | 7/1996 | Shima |
| 5,562,738 A | 10/1996 | Boyd et al. |
| 5,645,596 A | 7/1997 | Kim et al. |
| 5,645,601 A | 7/1997 | Pope et al. |
| 5,674,296 A | 10/1997 | Bryan et al. |
| 5,676,701 A | 10/1997 | Yuan et al. |
| 5,725,582 A | 3/1998 | Bevan et al. |
| 5,782,832 A | 7/1998 | Larsen et al. |
| 5,865,845 A | 2/1999 | Thalgott |
| 5,888,226 A | 3/1999 | Rogozinski |
| 5,895,428 A | 4/1999 | Berry |
| 5,899,941 A | 5/1999 | Nishijima et al. |
| 6,001,130 A | 12/1999 | Bryan et al. |
| 6,010,533 A | 1/2000 | Pope et al. |
| 6,019,792 A | 2/2000 | Cauthen |
| 6,039,763 A | 3/2000 | Shelokov |
| 6,113,637 A | 9/2000 | Gill et al. |
| 6,146,421 A | 11/2000 | Gordon et al. |
| 6,156,067 A | 12/2000 | Bryan et al. |
| 6,179,874 B1 | 1/2001 | Cauthen |
| 6,290,726 B1 | 9/2001 | Pope et al. |
| 6,368,350 B1 | 4/2002 | Erickson et al. |
| 6,398,815 B1 | 6/2002 | Pope et al. |
| 6,402,787 B1 | 6/2002 | Pope et al. |
| 6,410,877 B1 | 6/2002 | Dixon et al. |
| 6,425,920 B1 | 7/2002 | Hamada |
| 6,425,922 B1 | 7/2002 | Pope et al. |
| 6,488,715 B1 | 12/2002 | Pope et al. |
| 6,494,918 B1 | 12/2002 | Pope et al. |
| 6,497,727 B1 | 12/2002 | Pope et al. |
| 6,514,289 B1 | 2/2003 | Pope et al. |
| 6,517,580 B1 | 2/2003 | Ramadan et al. |
| 6,517,583 B1 | 2/2003 | Pope et al. |
| 6,520,993 B2 | 2/2003 | James et al. |
| 6,540,785 B1 | 4/2003 | Gill et al. |
| 6,596,225 B1 | 7/2003 | Pope et al. |
| 6,610,095 B1 | 8/2003 | Pope et al. |
| 6,655,845 B1 | 12/2003 | Pope et al. |
| 6,676,704 B1 | 1/2004 | Pope et al. |
| 6,682,562 B2 | 1/2004 | Viart et al. |
| 6,706,068 B2 | 3/2004 | Ferree |
| 6,709,463 B1 | 3/2004 | Pope et al. |
| 6,726,720 B2 | 4/2004 | Ross et al. |
| 6,740,118 B2 | 5/2004 | Eisermann et al. |
| 6,749,635 B1 | 6/2004 | Bryan |
| 6,770,095 B2 | 8/2004 | Grinberg et al. |
| 6,793,681 B1 | 9/2004 | Pope et al. |
| 6,800,095 B1 | 10/2004 | Pope et al. |
| 6,817,550 B2 | 11/2004 | Taylor et al. |
| 6,846,328 B2 | 1/2005 | Cauthen |
| 6,908,484 B2 | 6/2005 | Zubok et al. |
| 6,972,037 B2 | 12/2005 | Zubok et al. |
| 6,972,038 B2 | 12/2005 | Zubok et al. |
| 6,986,789 B2 | 1/2006 | Schultz et al. |
| 6,994,727 B2 | 2/2006 | Khandkar et al. |
| 6,994,728 B2 | 2/2006 | Zubok et al. |
| 6,994,729 B2 | 2/2006 | Zubok et al. |
| 6,994,954 B2 | 2/2006 | Zubok et al. |
| 6,997,955 B2 | 2/2006 | Zubok et al. |
| 7,001,433 B2 | 2/2006 | Songer et al. |
| 7,060,099 B2 | 6/2006 | Carli et al. |
| 7,066,958 B2 | 6/2006 | Ferree |
| 7,066,960 B1 | 6/2006 | Dickman |
| 7,077,867 B1 | 7/2006 | Pope et al. |
| 7,083,651 B2 | 8/2006 | Diaz et al. |
| 7,105,024 B2 | 9/2006 | Richelsoph |
| 7,118,580 B1 | 10/2006 | Beyersdorff et al. |
| 7,147,665 B1 | 12/2006 | Bryan et al. |
| 7,169,182 B2 | 1/2007 | Errico et al. |
| 7,172,142 B2 | 2/2007 | Taylor et al. |
| 7,198,643 B2 | 4/2007 | Zubok et al. |
| 7,223,291 B2 | 5/2007 | Errico et al. |
| 7,226,480 B2 | 6/2007 | Thalgott |
| 7,235,081 B2 | 6/2007 | Errico et al. |
| 7,270,679 B2 | 9/2007 | Istephanous et al. |
| 7,276,082 B2 | 10/2007 | Zdeblick et al. |
| 7,294,134 B2 | 11/2007 | Weber |
| 7,326,250 B2 | 2/2008 | Beaurain et al. |
| 7,338,527 B2 | 3/2008 | Blatt et al. |
| D566,842 S | 4/2008 | Robie |
| D567,377 S | 4/2008 | Blouin et al. |
| 7,396,501 B2 | 7/2008 | Pope et al. |
| 7,396,505 B2 | 7/2008 | Pope et al. |
| 7,442,211 B2 | 10/2008 | De Villiers et al. |
| D580,551 S | 11/2008 | Cohen et al. |
| D580,552 S | 11/2008 | Cohen et al. |
| 7,461,978 B2 | 12/2008 | Pope et al. |
| 7,465,219 B2 | 12/2008 | Dixon et al. |
| D585,552 S | 1/2009 | Blouin et al. |
| 7,491,241 B2 | 2/2009 | Errico et al. |
| 7,494,507 B2 | 2/2009 | Dixon et al. |
| 7,503,935 B2 | 3/2009 | Zucherman et al. |
| 7,537,615 B2 | 5/2009 | Lemaire |
| 7,549,995 B2 | 6/2009 | Schultz |
| 7,550,009 B2 | 6/2009 | Arnin et al. |
| D595,853 S | 7/2009 | Hanson et al. |
| 7,556,763 B2 | 7/2009 | Pope et al. |
| 7,569,067 B2 | 8/2009 | Keller |
| 7,569,176 B2 | 8/2009 | Pope et al. |
| 7,575,576 B2 | 8/2009 | Zubok et al. |
| 7,594,919 B2 | 9/2009 | Peterman |
| 7,608,080 B2 | 10/2009 | Shipp et al. |
| 7,611,538 B2 | 11/2009 | Belliard et al. |
| 7,618,459 B2 | 11/2009 | Justin et al. |
| 7,628,814 B2 | 12/2009 | Studer et al. |
| 7,632,281 B2 | 12/2009 | Errico et al. |
| 7,635,368 B2 | 12/2009 | Errico et al. |
| 7,637,952 B2 | 12/2009 | Landry et al. |
| 7,637,955 B2 | 12/2009 | Marik et al. |
| 7,637,956 B2 | 12/2009 | Lechmann et al. |
| 7,655,045 B2 | 2/2010 | Richelsoph |
| 7,665,898 B2 | 2/2010 | Pope et al. |
| 7,678,325 B2 | 3/2010 | Gardinier |
| 7,691,146 B2 | 4/2010 | Zucherman et al. |
| 7,708,780 B2 | 4/2010 | Zubok et al. |
| 7,713,304 B2 | 5/2010 | Ankney et al. |
| 7,806,901 B2 | 10/2010 | Stad et al. |
| 7,811,287 B2 | 10/2010 | Errico et al. |
| 7,811,329 B2 | 10/2010 | Ankney et al. |
| 7,927,374 B2 | 4/2011 | Duggal et al. |
| 8,016,889 B2 | 9/2011 | Dixon et al. |
| 8,021,428 B2 | 9/2011 | Bartish, Jr. et al. |
| 8,038,716 B2 | 10/2011 | Duggal et al. |
| 8,092,538 B2 | 1/2012 | De Villiers et al. |
| 8,100,974 B2 | 1/2012 | Duggal et al. |
| 8,163,023 B2 | 4/2012 | Nguyen et al. |
| 8,172,904 B2 | 5/2012 | Duggal et al. |
| 8,449,991 B2 | 5/2013 | Gardinier et al. |
| 8,535,326 B2 * | 9/2013 | Beyersdorff ......... A61F 2/4611 606/99 |
| 8,535,379 B2 | 9/2013 | Moskowitz et al. |
| 8,603,169 B2 | 12/2013 | Nguyen et al. |
| 8,603,181 B2 | 12/2013 | Pope et al. |
| 8,663,359 B2 | 3/2014 | Harding et al. |
| 9,078,763 B2 | 7/2015 | Nguyen et al. |
| 2003/0019106 A1 | 1/2003 | Pope et al. |
| 2003/0078660 A1 | 4/2003 | Clifford et al. |
| 2003/0191533 A1 | 10/2003 | Dixon et al. |
| 2004/0002761 A1 | 1/2004 | Rogers et al. |
| 2004/0111159 A1 | 6/2004 | Pope et al. |
| 2004/0143332 A1 | 7/2004 | Krueger et al. |
| 2004/0153158 A1 | 8/2004 | Errico et al. |
| 2004/0199260 A1 | 10/2004 | Pope et al. |
| 2004/0223676 A1 | 11/2004 | Pope et al. |
| 2004/0243241 A1 | 12/2004 | Istephanous |
| 2005/0015095 A1 | 1/2005 | Keller |
| 2005/0033438 A1 | 2/2005 | Schultz et al. |
| 2005/0043802 A1 | 2/2005 | Eisermann et al. |
| 2005/0055095 A1 | 3/2005 | Errico et al. |
| 2005/0055098 A1 | 3/2005 | Zdeblick et al. |
| 2005/0080487 A1 | 4/2005 | Schultz et al. |
| 2005/0087915 A1 | 4/2005 | Pope et al. |

(56) References Cited

U.S. PATENT DOCUMENTS

| | | |
|---|---|---|
| 2005/0110187 A1 | 5/2005 | Pope et al. |
| 2005/0121417 A1 | 6/2005 | Dixon et al. |
| 2005/0123824 A1 | 6/2005 | Richelsoph et al. |
| 2005/0133277 A1 | 6/2005 | Dixon et al. |
| 2005/0143820 A1 | 6/2005 | Zucherman |
| 2005/0146086 A1 | 7/2005 | Pope et al. |
| 2005/0149196 A1 | 7/2005 | Zucherman et al. |
| 2005/0158200 A1 | 7/2005 | Pope et al. |
| 2005/0165487 A1 | 7/2005 | Muhanna et al. |
| 2005/0171610 A1 | 8/2005 | Humphreys et al. |
| 2005/0187633 A1 | 8/2005 | Ferree |
| 2005/0197705 A1 | 9/2005 | Arnin et al. |
| 2005/0203626 A1 | 9/2005 | Sears et al. |
| 2005/0203630 A1 | 9/2005 | Pope et al. |
| 2005/0216092 A1 | 9/2005 | Marik et al. |
| 2005/0228497 A1 | 10/2005 | Ferree et al. |
| 2005/0240270 A1 | 10/2005 | Zubok et al. |
| 2005/0240271 A1 | 10/2005 | Zubok et al. |
| 2005/0240272 A1 | 10/2005 | Zubok et al. |
| 2005/0256577 A1 | 11/2005 | Baumgartner et al. |
| 2005/0256578 A1 | 11/2005 | Blatt et al. |
| 2005/0267582 A1 | 12/2005 | Ferree et al. |
| 2006/0004453 A1 | 1/2006 | Bartish, Jr. et al. |
| 2006/0020342 A1 | 1/2006 | Ferree et al. |
| 2006/0036327 A1 | 2/2006 | Enayati |
| 2006/0041313 A1 | 2/2006 | Allard et al. |
| 2006/0069439 A1 | 3/2006 | Zucherman et al. |
| 2006/0069440 A1 | 3/2006 | Zucherman et al. |
| 2006/0069441 A1 | 3/2006 | Zucherman et al. |
| 2006/0085076 A1 | 4/2006 | Krishna et al. |
| 2006/0085077 A1 | 4/2006 | Cook et al. |
| 2006/0116768 A1 | 6/2006 | Krueger et al. |
| 2006/0149372 A1 | 7/2006 | Paxson et al. |
| 2006/0178745 A1 | 8/2006 | Bartish, Jr. et al. |
| 2006/0212122 A1 | 9/2006 | Perera |
| 2006/0235530 A1 | 10/2006 | Shelokov |
| 2006/0247777 A1 | 11/2006 | Stamp |
| 2006/0259147 A1 | 11/2006 | Krishna et al. |
| 2006/0263233 A1 | 11/2006 | Gardinier et al. |
| 2006/0265074 A1 | 11/2006 | Krishna et al. |
| 2006/0282020 A1 | 12/2006 | Bertagnoli et al. |
| 2007/0010887 A1 | 1/2007 | Williams et al. |
| 2007/0016302 A1 | 1/2007 | Dickman |
| 2007/0021836 A1 | 1/2007 | Doty et al. |
| 2007/0100454 A1 | 5/2007 | Burgess et al. |
| 2007/0118224 A1 | 5/2007 | Shah et al. |
| 2007/0123985 A1 | 5/2007 | Errico et al. |
| 2007/0156243 A1 | 7/2007 | Errico et al. |
| 2007/0168037 A1 | 7/2007 | Posnik |
| 2007/0168040 A1 | 7/2007 | Raymond |
| 2007/0173941 A1 | 7/2007 | Allard |
| 2007/0173942 A1 | 7/2007 | Heinz et al. |
| 2007/0179614 A1 | 8/2007 | Heinz et al. |
| 2007/0179615 A1 | 8/2007 | Heinz et al. |
| 2007/0179618 A1 | 8/2007 | Trieu et al. |
| 2007/0191952 A1 | 8/2007 | Bernero |
| 2007/0198092 A1 | 8/2007 | Errico et al. |
| 2007/0208426 A1 | 9/2007 | Trieu |
| 2007/0233262 A1 | 10/2007 | Arnin et al. |
| 2007/0250168 A1 | 10/2007 | Lechmann et al. |
| 2007/0270970 A1 | 11/2007 | Trieu |
| 2007/0270971 A1 | 11/2007 | Trieu et al. |
| 2007/0276492 A1 | 11/2007 | Andrews et al. |
| 2008/0021557 A1 | 1/2008 | Trieu |
| 2008/0114453 A1 | 5/2008 | Francis |
| 2008/0119932 A1 | 5/2008 | Lechmann et al. |
| 2008/0140204 A1 | 6/2008 | Heinz |
| 2008/0154380 A1 | 6/2008 | Dixon et al. |
| 2008/0161821 A1 | 7/2008 | Heinz |
| 2008/0161925 A1 | 7/2008 | Brittan et al. |
| 2008/0177299 A1 | 7/2008 | Kim et al. |
| 2008/0195212 A1 | 8/2008 | Nguyen et al. |
| 2008/0195220 A1 | 8/2008 | Pope et al. |
| 2008/0215158 A1 | 9/2008 | Pope et al. |
| 2008/0221693 A1 | 9/2008 | Brehm et al. |
| 2008/0221696 A1 | 9/2008 | De Villiers et al. |
| 2008/0294259 A1 | 11/2008 | De Villiers et al. |
| 2008/0300685 A1 | 12/2008 | Carls et al. |
| 2009/0012619 A1 | 1/2009 | Cordaro et al. |
| 2009/0030421 A1 | 1/2009 | Hawkins et al. |
| 2009/0030422 A1 | 1/2009 | Parsons et al. |
| 2009/0043393 A1 | 2/2009 | Duggal et al. |
| 2009/0088856 A1 | 4/2009 | Levieux |
| 2009/0132049 A1 | 5/2009 | Carver et al. |
| 2009/0248161 A1 | 10/2009 | Theofilos et al. |
| 2009/0263643 A1 | 10/2009 | Gardinier et al. |
| 2009/0270986 A1 | 10/2009 | Christensen |
| 2009/0270988 A1 | 10/2009 | Snell et al. |
| 2009/0326542 A9 | 12/2009 | Errico et al. |
| 2009/0326656 A1 | 12/2009 | De Villiers et al. |
| 2009/0326658 A1 | 12/2009 | Allard |
| 2010/0004657 A1 | 1/2010 | Dudasik |
| 2010/0004746 A1 | 1/2010 | Arramon |
| 2010/0016972 A1 | 1/2010 | Jansen et al. |
| 2010/0023019 A1 | 1/2010 | Fuhrer et al. |
| 2010/0025898 A1 | 2/2010 | Pope et al. |
| 2010/0049323 A1 | 2/2010 | Gill et al. |
| 2010/0100141 A1 | 4/2010 | de Villiers et al. |
| 2010/0174371 A9 | 7/2010 | Errico et al. |
| 2010/0179660 A1 | 7/2010 | Peukert et al. |
| 2010/0191338 A1 | 7/2010 | De Villiers et al. |
| 2010/0198353 A1 | 8/2010 | Pope et al. |
| 2010/0228351 A1 | 9/2010 | Ankney et al. |
| 2010/0249795 A1 | 9/2010 | DiMauro et al. |
| 2010/0280618 A1 | 11/2010 | Jodaitis et al. |
| 2010/0286784 A1 | 11/2010 | Curran et al. |
| 2010/0292800 A1 | 11/2010 | Zubok |
| 2010/0324684 A1 | 12/2010 | Eisermann et al. |
| 2011/0082556 A1 | 4/2011 | Duggal et al. |
| 2011/0087331 A1 | 4/2011 | Reichen et al. |
| 2011/0098821 A1 | 4/2011 | Ankney et al. |
| 2011/0137421 A1 | 6/2011 | Hansell et al. |
| 2011/0146348 A1 | 6/2011 | Harding et al. |
| 2011/0160862 A1 | 6/2011 | De Villiers et al. |
| 2011/0257747 A1 | 10/2011 | Copf |
| 2011/0301612 A1 | 12/2011 | Richter et al. |
| 2011/0320003 A1 | 12/2011 | Duggal et al. |
| 2012/0035732 A1 | 2/2012 | De Villiers et al. |
| 2012/0232661 A1 | 9/2012 | Nguyen et al. |
| 2013/0260173 A1 | 10/2013 | Gardinier et al. |
| 2014/0172100 A1 | 6/2014 | Nguyen et al. |
| 2014/0315038 A1 | 10/2014 | Harding et al. |
| 2015/0374505 A1 | 12/2015 | Nguyen et al. |

FOREIGN PATENT DOCUMENTS

| | | |
|---|---|---|
| JP | 11-137585 | 5/1999 |
| JP | 2002-508679 | 3/2002 |
| JP | 2004-329937 | 11/2004 |
| JP | 2005-523109 | 8/2005 |
| JP | 2006-510452 | 3/2006 |
| KR | 20120126264 | 11/2012 |
| RU | 2212865 | 9/2003 |
| WO | WO 94/04100 | 3/1994 |
| WO | WO 2005/025431 | 3/2005 |
| WO | WO 2005/089680 | 9/2005 |
| WO | WO 2006/130086 | 12/2006 |
| WO | WO 2007/118119 | 10/2007 |
| WO | WO 2007/133553 | 11/2007 |
| WO | WO 2009/149371 | 12/2009 |

* cited by examiner

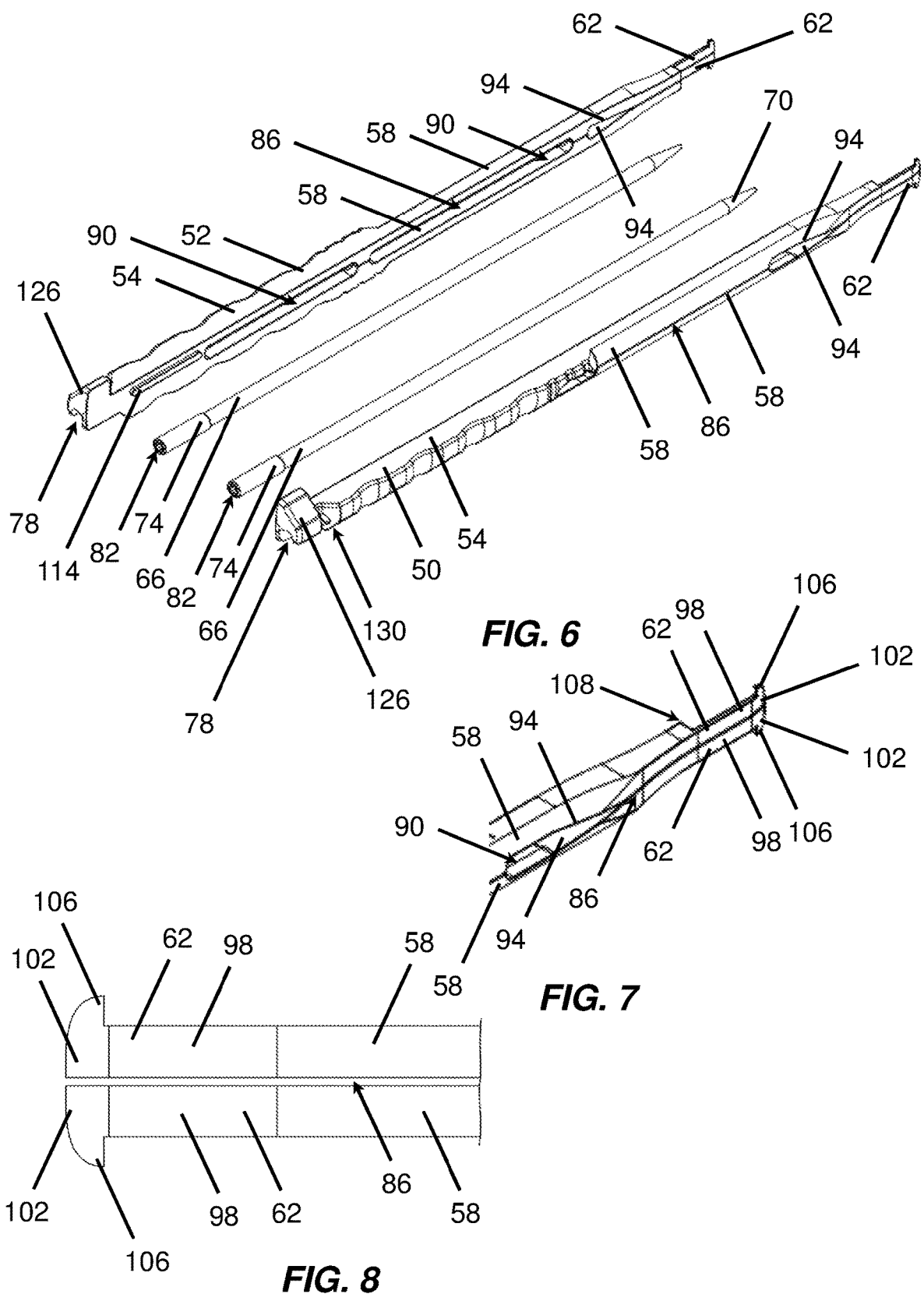

SPINAL ARTIFICIAL DISC REMOVAL TOOL

PRIORITY

The present application claims the benefit of U.S. Provisional Application Ser. No. 62/904,680, filed Sep. 23, 2019, which is herein incorporated by reference in its entirety.

THE FIELD OF THE INVENTION

The present invention relates to artificial spinal discs. In particular, examples of the present invention relate to a tool for removing an installed artificial spinal disc.

BACKGROUND

Various companies have developed artificial discs to replace damaged spinal discs. These artificial discs preserve mobility in the spine and are frequently preferable to fusion of the vertebrae. In some instances, it becomes necessary to remove an artificial disc. This may occur during surgery or after installation of an artificial disc.

BRIEF DESCRIPTION OF THE DRAWINGS

Non-limiting and non-exhaustive examples of the present invention are described with reference to the following figures, wherein like reference numerals refer to like parts throughout the various views unless otherwise specified.

FIG. 6 is a drawing showing an exploded perspective view of the artificial disc extraction tool.
FIG. 7 is a perspective drawing of the artificial disc extraction tool tines.
FIG. 8 is a drawing of the artificial disc extraction tool tines.

Figure 1:
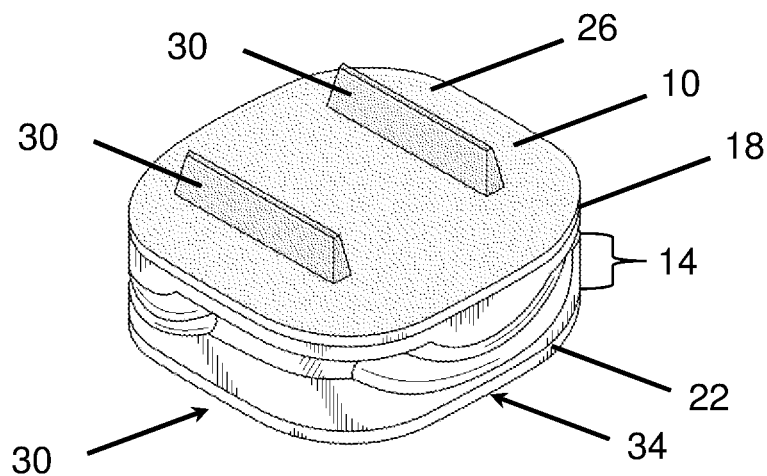
FIG. 1 is a drawing of an artificial spinal disc.

Corresponding reference characters indicate corresponding components throughout the several views of the drawings. Unless otherwise noted, the drawings have been drawn to scale. Skilled artisans will appreciate that elements in the figures are illustrated for simplicity and clarity. For example, the dimensions of some of the elements in the figures may be exaggerated relative to other elements to help improve understanding of various examples of the present invention. Also, common but well-understood elements that are useful or necessary in a commercially feasible embodiment are often not depicted in order to facilitate a less obstructed view of these various embodiments of the present invention.

It will be appreciated that the drawings are illustrative and not limiting of the scope of the invention which is defined by the appended claims. The examples shown each accomplish various different advantages. It is appreciated that it is not possible to clearly show each element or advantage in a single figure, and as such, multiple figures are presented to separately illustrate the various details of the examples in greater clarity. Similarly, not every example need accomplish all advantages of the present disclosure.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

In the above disclosure, reference has been made to the accompanying drawings, which form a part hereof, and in which are shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, such feature, structure, or characteristic may be used in connection with other embodiments whether or not explicitly described. The particular features, structures or characteristics may be combined in any suitable combination and/or sub-combinations in one or more embodiments or examples. It is appreciated that the figures provided herewith are for explanation purposes to persons ordinarily skilled in the art.

As used herein, "adjacent" refers to near or close sufficient to achieve a desired effect. Although direct contact is common, adjacent can broadly allow for spaced apart features.

As used herein, the singular forms "a," and, "the" include plural referents unless the context clearly dictates otherwise.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a number or numerical range endpoint by providing that a given value may be "a little above" or "a little below" the number or endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Dimensions, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

Artificial spinal discs may be installed surgically to replace a damaged spinal disc. Generally, a damaged spinal disc may be treated by fusing the adjacent vertebrae together or by replacing the disc with an artificial disc. As more sophisticated spinal discs are developed by various medical device companies, replacement of a damaged disc with an artificial disc is increasingly preferable to fusion of adjacent vertebrae as it preserves a degree of motion at that location within the spine. Surgeries to install artificial discs have a degree of unpredictability which may not be observed from pre-operative examination. Variable condition of the bone and surgical site, for example, may be observed by the surgeon. In some situations, it has become necessary to remove an installed artificial spinal disc from a patient. This may occur during the original surgical procedure to install the artificial spinal disc. For example, continued bleeding from the bone surfaces of the vertebrae may require removal of an installed artificial disc. The surgeon may then perform additional treatment procedures and reinstall the artificial disc.

Turning now to FIG. 1, a perspective view of an artificial (prosthetic) disc 10 used to replace a damaged spinal disc is shown. The artificial disc 10 includes an articular body 14 which includes components that interact with each other to provide articulating motion to the artificial disc. The articular body 14 may include an upper and a lower articulation surface, an elastomeric articulation component, etc. Companies have created artificial discs with different types of articular bodies 14 including a ball in socket joint, a ball in trough joint, elastomeric joints, and complex articulation surfaces. The articular body 14 as described is often formed by part of the upper portion 18 of the artificial disc 10 and part of the lower portion 22 of the artificial disc. 10. The articular body 14 may also include an additional component located between the upper portion 18 and lower portion 22 of the artificial disc 10 such as an elastomeric component or a core.

The upper portion 18, or upper plate, of the artificial disc 10 typically attaches to or includes part of the articular body 14 and includes an upper bone attachment surface 26. The upper bone attachment surface 26 often includes one or two keels 30 to aid in fixation of the upper portion 18 and an adjacent vertebra. The upper keels 30 extend upwardly from the upper portion 18 of the artificial disc 10. The bone attachment surface 26 may be treated to provide initial mechanical grip for initial bone fixation and also allows for bone ingrowth (osseointegration) for long term fixation of the artificial disc 10. The bone attachment surface 26 may be roughened or include a rough titanium plasma coating, bead coating, or particulate coating that provides the mechanical grip and allows for bone ingrowth. The lower portion 22, or lower plate, of the artificial disc 10 typically attaches to or includes part of the articular body 14 and a lower bone attachment surface 34. The lower bone attachment surface also includes one or two keels 30 to aid in fixation of the lower portion 22 to an adjacent vertebra. The lower keels 30 extend downwardly from the lower portion 22 of the artificial disc 10. The bone attachment surface 34 may be treated to provide mechanical grip and to allow for bone ingrowth. The bone attachment surface 34 may be roughened or include a rough titanium plasma coating, bead coating, or particulate coating that provides the mechanical grip and allows for bone ingrowth.

Figure 2:
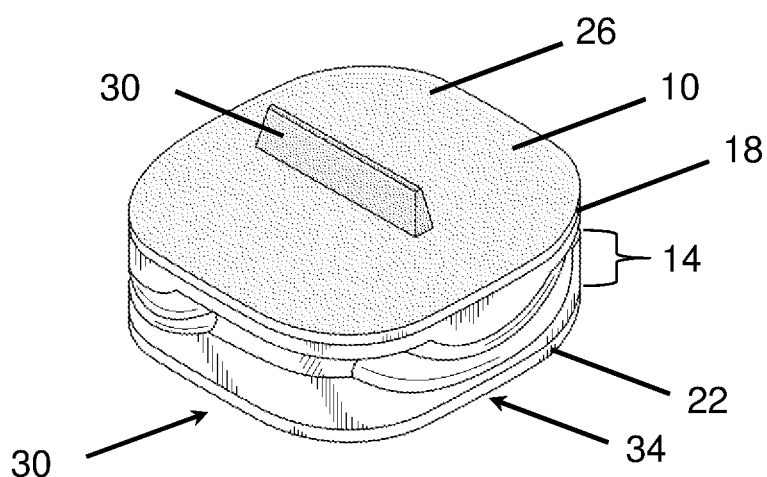
FIG. 2 is a drawing of an artificial spinal disc.

For an artificial disc 10 such as a ball in socket joint or a joint with a complex articular surface, the upper portion 18 may be an upper plate which is configured to attach to a vertebra above the installed artificial disc 10. The upper portion 18 may include an upper attachment surface 26 with an upper keel 30. The upper part of the articular body 14, such as a ball or complex articulation surface, may be formed as part of the upper portion 18. The lower portion 22 may be a lower plate which is configured to attach to a vertebra below the installed artificial disc 10. The lower portion 22 may include a lower attachment surface 34 with a lower keel 30. The lower part of the articular body 14, such as a socket or trough or a complex articulation surface, may be formed as part of the lower portion 22. The upper portion 18 and lower portion 22 may contact each other and provide articulation motion therebetween in an installed disc 10 to provide the desired motion to the patient. FIG. 1 shows an artificial disc 10 with two keels 30 on each bone attachment surface 26, 34. FIG. 2 shows a similar artificial disc 10 which differs in that it includes a single keel 30 on each bone attachment surface 26, 34.

Figure 3:
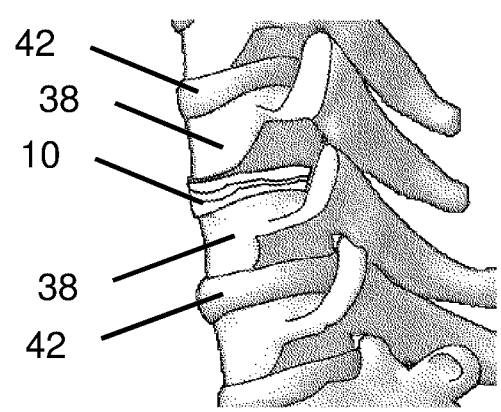
FIG. 3 is a drawing of an artificial disc installed in a spine.

FIG. 3 shows a lateral view of an installed artificial spinal disc 10. The artificial disc 10 is installed between two vertebrae 38 to replace a natural spinal disc (e.g. 42) which is damaged. For an example cervical disc, an anterior incision is made in the neck and ligaments and muscles are retracted to expose the damaged spinal disc. The damaged natural disc and cartilage are removed and disc height is restored. Slots are created in the vertebrae 38 to receive the keels 30 of the artificial discs 10. The artificial disc 10 is installed between the prepared vertebrae 38; placing the keel 30 into the slots in the vertebrae 38. The keels 30 and surface of the bone attachment surfaces 26, 34 provide short term fixation of the artificial spinal disc 10 and secure the artificial disc 10 to the vertebrae 38.

Figure 4:
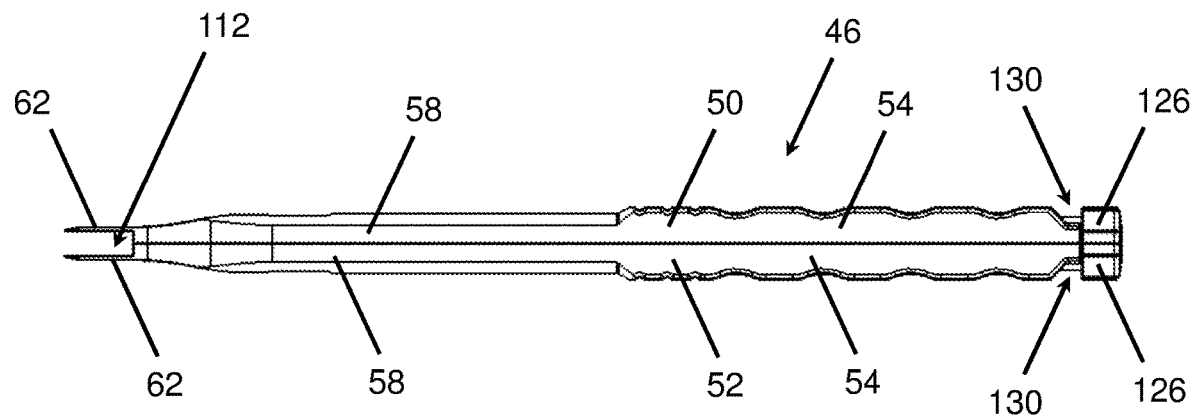
FIG. 4 is a drawing showing a side view of an artificial disc extraction tool for removing an installed artificial disc from a spine.
Figure 5:
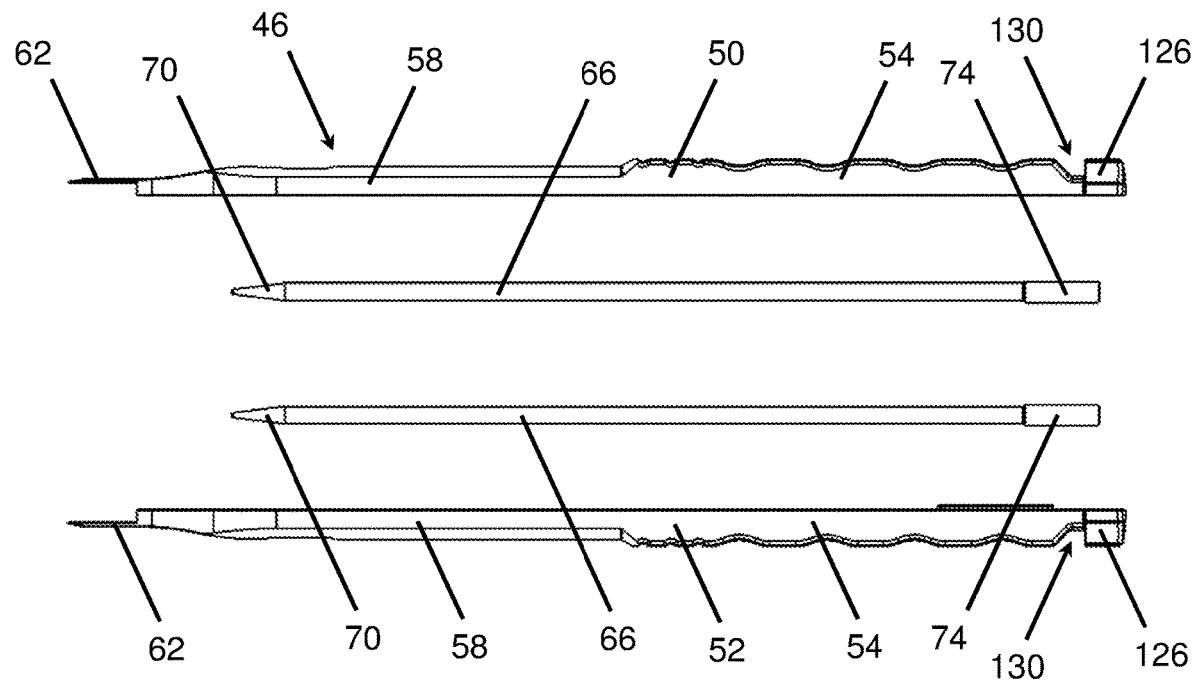
FIG. 5 is a drawing showing an exploded side view of the artificial disc extraction tool.

In some cases, it becomes necessary to remove the artificial disc 10 after installation. There may be continued bleeding from the vertebrae, for example, which necessitates removal of the artificial disc 10 and correction before finishing the disc replacement surgery. FIGS. 4 through 6 show an artificial spinal disc extraction tool 46. FIG. 4 shows a side view of the extraction tool 46. FIG. 5 shows an exploded side view of the extraction tool 46. FIG. 6 shows an exploded perspective view of the extraction tool 46.

The extraction tool 46 includes an upper extraction tool member 50 and a lower extraction tool member 52 which are separable from each other. The upper extraction tool member 50 and the lower extraction tool member 52 are attachable together during use and an artificial disc 10 is typically extracted after the extraction tool 46 is attached together in the configuration shown in FIG. 4. The upper extraction tool member 50 and the lower extraction tool member 52 each includes a body 54, arms 58 which extend distally from the body 54, and tines 62 disposed at the distal end of the arms 58. Each extraction tool member 50, 52 includes two arms 58 which extend distally from the body 54 and each arm 58 includes a tine 62 on its end so that each extraction tool member includes two tines 62. For each extraction tool member 50, 52, the arms 58 may pivot or flex away from each other or towards each other to engage or disengage the artificial disc keels 30.

Each extraction tool member 50, 52 includes an actuator, such as expansion pin 66 with a tapered distal end 70 and a threaded section 74 typically disposed on the proximal end of the expansion pin 66. The expansion pin 66 is located in a channel or bore formed through the extraction tool member 50, 52. The threaded section 74 of each expansion pin 66 engages a correspondingly threaded receiver 78 on the extraction tool member 50, 52. In the example extraction tool 46, the threaded sections 74 and threaded receivers 78 are disposed at the proximal ends of the expansion pins 66 and the bodies 54 of each extraction tool member 50, 52. The proximal ends of the expansion pins 66 include a drive socket 82 such as a hex socket or Torx socket. This allows a user to turn the expansion pins 66 with a drive tool to advance or retract the expansion pins 66 within the extraction tool member 50, 52.

As is visible in FIG. 6, each extraction tool member 50, 52 includes a slot 86 which extends lengthwise through approximately the distal half of the extraction tool member and separates the two arms 58 and tines 62. The slot 86 allows the arms 58 and tines 62 to flex and move towards or away from each other. Generally, the slot 86 extends through the tines 62 and arms 58 and does not extend through the body section 54. The expansion pins 66 extend through a channel 90 through the actuator tool member 50, 52. The distal end of each arm 58 includes an angled ramp 94 such that each extraction tool member 50, 52 includes a pair of angled ramps 94. The angled ramps 94 are disposed opposite each other and are disposed on the distal ends of the arms 58 hear the tines 62. The faces of the angled ramps 94 define an included angle therebetween which is approximately equal to the angle of the tapered distal ends 70 of the expansion pins 66. When the expansion pins 66 are placed within each extraction tool member 50, 52, the threaded section 74 of the expansion pin engages the threaded receiver 78 of the body 54 and the tapered distal ends 70 are disposed adjacent the angled ramps 94. Using a drive tool to rotate the expansion pins 66 clockwise advances the expansion pins 66 distally within the extraction tool member 50, 52 and forces the tapered distal end 70 to advance between the angled ramps 94; spreading the arms 58 and tines 62 apart from each other. Using the drive tool to rotate the expansion pins 66 counterclockwise retracts the expansion pins 66 and moves the tapered ends 70 proximally away from the angled ramps 94; allowing the tines 62 to move towards each other.

FIG. 7 shows a more detailed perspective view of a pair of tines 62 on one extraction tool member 50, 52. FIG. 8 shows a more detailed top view of the pair of tines 62. Each tine 62 includes a thin tine body 98 with a tip 102. The tine body 98 is made thin as it is driven between the installed artificial disc 10 and the vertebra 38 during use. One outside face of the tip 102 of each tine 62 is beveled and tapers such that the distal end of the tine body 98 is thinner than the proximal tine body 98. As is visible in FIG. 4, the tine 62 is flat on the side which faces the artificial disc 10 and the tapered face of the tip 102 is located on the side of the tine body 98 which faces away from the artificial disc 10 in use. The tip 102 is shaped so that the flat inner side slides along the bone attachment surface 26, 34 of the artificial disc 10 and the tapered face of the tip 102 slides along the prepared surface of the vertebra 38; minimizing damage to the bone and wedging between the bone 38 and the artificial disc 10 to dislodge the keels 30 from the bone. Each tip 102 includes a keel tab 106 which is angled relative to the tine body 98 and which extends laterally away from the tine body 98. Each keel tab 106 forms a small angular notch on the side of each tine 62. The tine body 98 is spaced apart from the middle of the artificial disc extraction tool 46 by a distance indicated generally at 108 which is approximately equal to half of the thickness of the artificial disc 10. This creates a space 112 (FIG. 4) between tines 62 in the assembled extraction tool 46 which receives an artificial disc 10.

Figure 9:
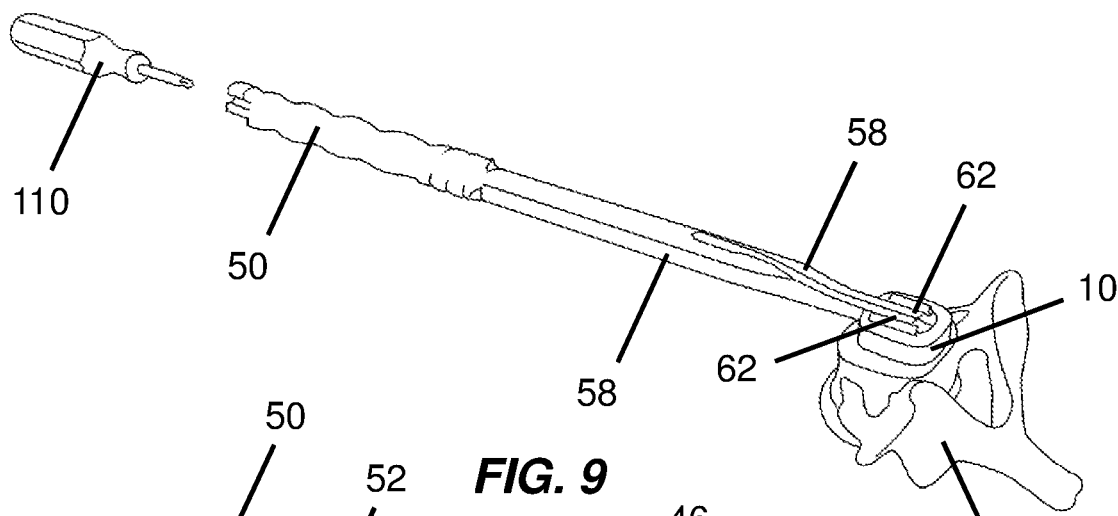
FIG. 9 is a drawing showing the use of the artificial disc extraction tool.

In use, the surgeon will typically start with each extraction tool member 50, 52 separated from each other and with the expansion pins 66 retracted so that the arms 58 and tines 62 are positioned towards each other as shown in FIG. 7. One extraction tool member 50, 52 (such as the upper member 50) is driven between the installed artificial disc 10 (e.g. the top) and the adjacent vertebra 38 as is shown in FIG. 9. The extraction tool member 50 is moved into this position by moving the tines 62 between the keels 30 of the artificial disc 10 until the keel tabs 106 are past the keels 30. A driver tool 110 is used to advance the expansion pin 66 and move the tines 62 apart from each other by wedging the tapered distal end 70 of the pin 66 between the angled ramps 94. This moves the tine keel tabs 106 apart laterally and moves them past the keels 30. If desired, the expansion pin 66 may be advanced until the tine bodies 98 are pressed against the inside edges of the keels 30 to stabilize the extraction tool member 50.

Figure 10:
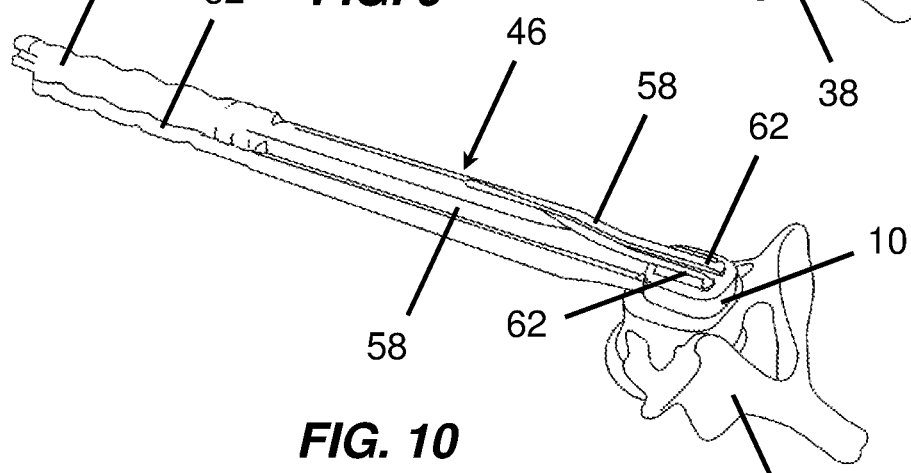
FIG. 10 is a drawing showing the use of the artificial disc extraction tool.
Figure 11:
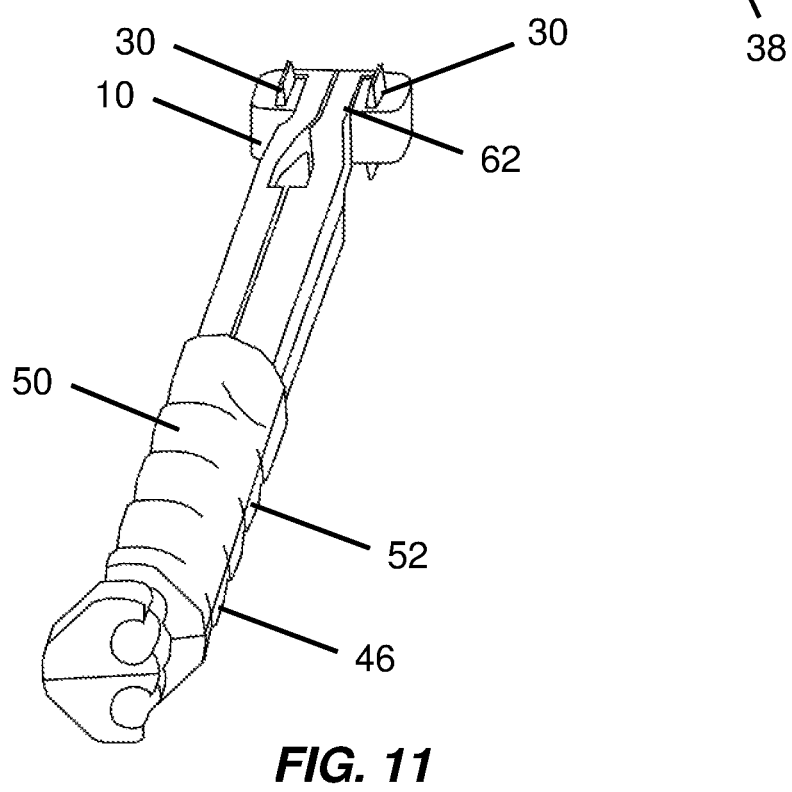
FIG. 11 is a drawing showing the use of the artificial disc extraction tool.

The second extraction tool member 52 is then driven between the other side (e.g. the bottom) of the installed artificial disc 10 and the adjacent vertebra 38. The extraction tool member 52 is moved into this position by moving the tines 62 between the keels 30 of the artificial disc 10 until the keel tabs 106 are past the keels 30. The two extraction tool halves 50, 52 are then attached to each other, such as by engaging a tab 114 (FIG. 6) on one extraction tool member 52 with a corresponding slot on the other extraction tool member 50. The driver tool 110 is used to advance the expansion pin 66 and move the tines 62 apart from each other by wedging the tapered distal end 70 of the pin 66 between the angled ramps 94. This moves the tine keel tabs 106 apart laterally and moves them past the keels 30. If desired, the expansion pin 66 may be advanced until the tine bodies 98 are pressed against the inside edges of the keels 30 to stabilize the extraction tool member 50. The artificial spinal disc extraction tool 46 is now in the configuration shown in FIG. 10. The extraction tool 46 may alternatively be attached to an installed artificial spinal disc 10 by driving the first extraction tool member 50 between the artificial disc 10 and a vertebra 38, driving the second extraction tool member 52 between the artificial disc and a vertebra 38, connecting the extraction tool halves 50, 52 together, and then expanding the tines 62 to engage the keels 30. FIG. 11 shows a perspective view of the extraction tool 46 without expanding the tines 62 to illustrate how the tines 62 fit between the keels 30 of an artificial disc 10.

Figure 12:
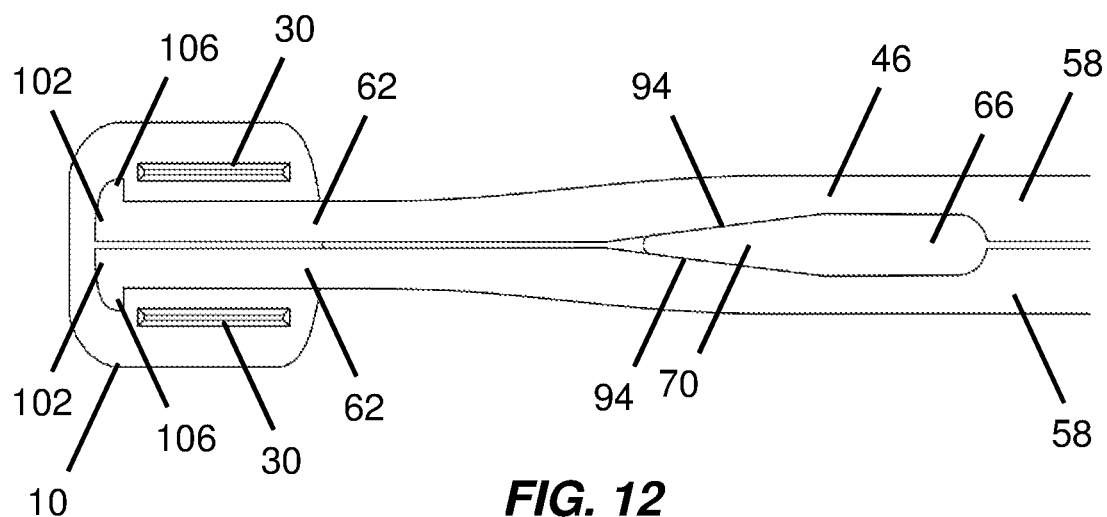
FIG. 12 is a drawing showing the use of the artificial disc extraction tool.
Figure 13:
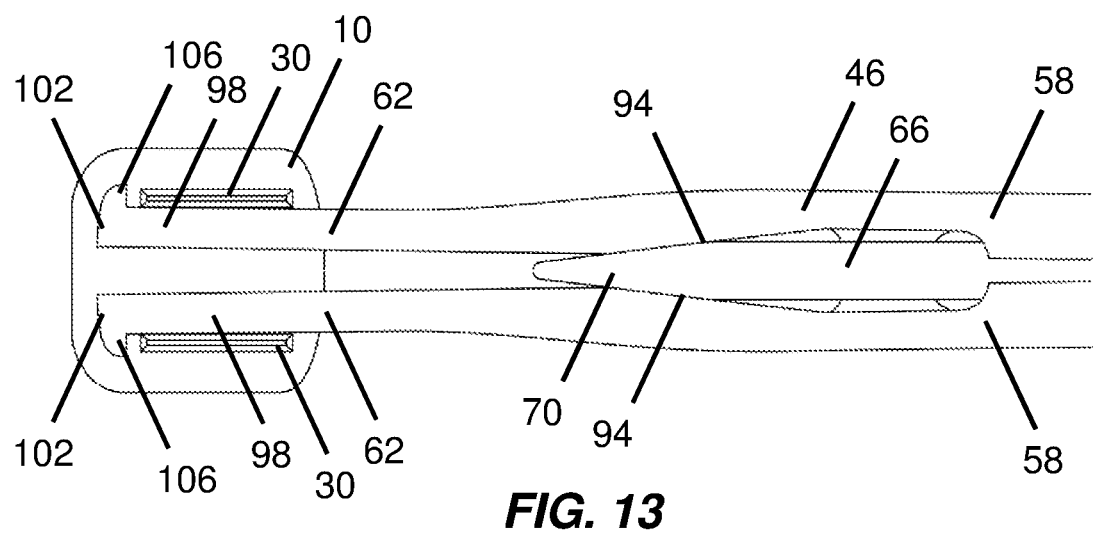
FIG. 13 is a drawing showing the use of the artificial disc extraction tool.

FIG. 12 shows a drawing of the tines 62 and artificial disc 10. The tines 62 are shown how they would be positioned after driving them between the artificial disc 10 and a vertebra 38 and before the tines 62 have been expended. FIG. 13 shows the extraction tool tines 62 after the expansion pin 66 has been advanced forwards to expand the tines 62. The tapered distal end 70 of the expansion pin 66 has been forced between the angled ramps 94; moving the tines 62 apart to engage the keels 30.

Figure 14:
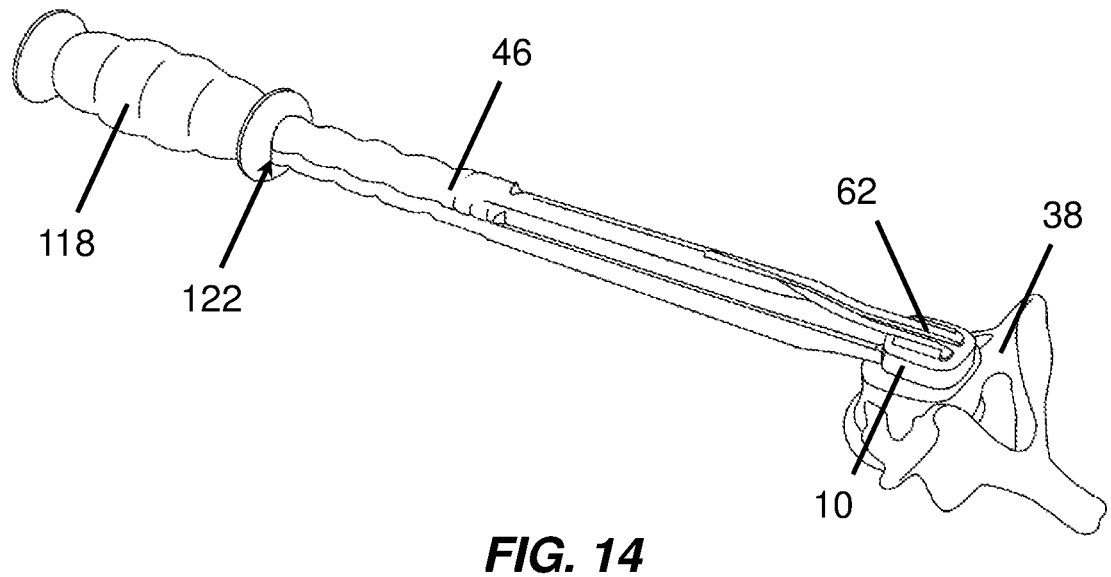
FIG. 14 is a drawing showing the use of the artificial disc extraction tool.

Once the tines 62 of both extraction tool halves 50, 52 are expanded against the keels 30 as shown in FIG. 13, a handle or slap hammer 118 may be attached to the extraction tool 46 as is shown in FIG. 14. The slap hammer 118 has a keyway slot 122 formed in one end of the slap hammer 118. The keyway slot 122 is attached to shoulders 126 and a recess 130 (FIGS. 4-6) formed at the proximal ends of the body 54 of each extraction tool member 50, 52. The slap hammer 118 may be used to pull the artificial disc 10 from between the vertebrae 38. The keel tabs 106 formed on the tines 62 engage the keels 30 and pull the artificial disc from the vertebrae 38. Both the upper portion 18 and the lower portion 22 of the artificial disc 10 are removed simultaneously from the spine. The extraction tool 46 may then be disassembled to release the artificial disc 10.

Figure 15:
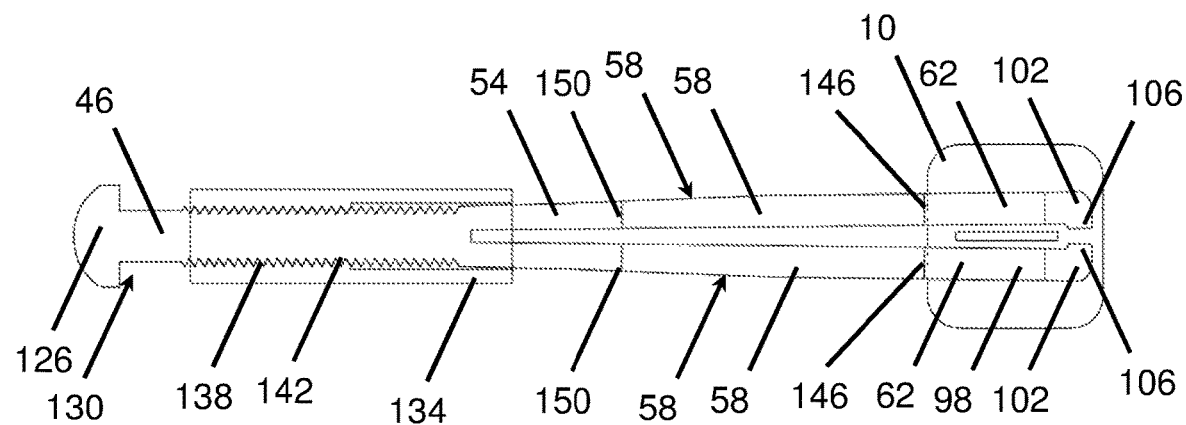
FIG. 15 is a drawing showing a top view of an artificial disc extraction tool.
Figure 16:
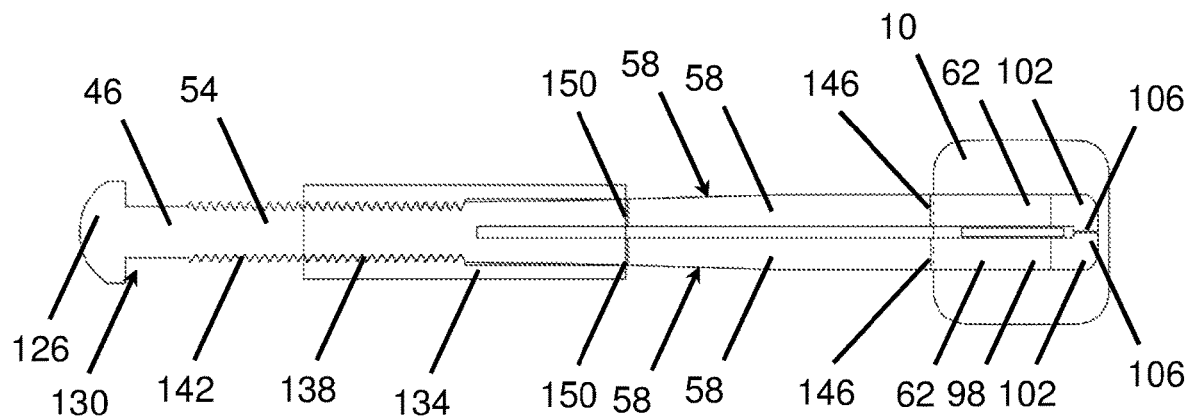
FIG. 16 is a drawing showing a top view of the artificial disc extraction tool of FIG. 15.
Figure 17:
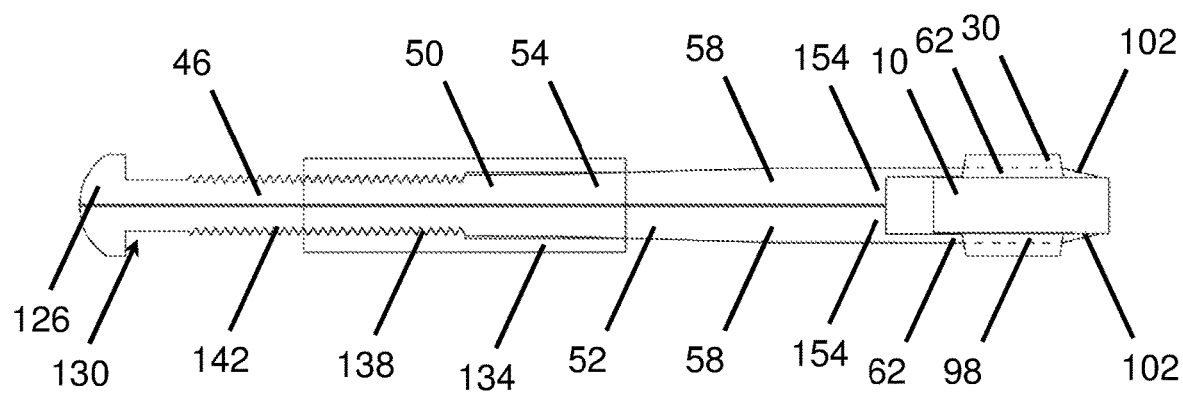
FIG. 17 is a drawing showing a side view of the artificial disc extraction tool of FIG. 15.

FIG. 15 through 17 show an extraction tool 46 configured to extract an artificial disc 10 with a single keel 30 on each of the top and bottom of the artificial disc 10. FIG. 15 shows a top view of the extraction tool 46 with the tines 62 expanded in an insertion position. FIG. 16 shows a top view of the extraction tool 46 with the tines 62 moved inwardly in a closed position where they capture the keels 30. FIG. 17 shows a side view of the extraction tool 46. The extraction tool 46 functions as discussed above except as otherwise noted. The extraction tool 46 includes a body 54, two upper arms 58 which extend distally from the body 54, and two tines 62 disposed at the distal end of the arms 58. The extraction tool 46 also includes two lower arms 58 with two tines 62 disposed at the distal ends of the lower arms. The upper tines 62 are inserted above the artificial disc 10 and the lower tines 62 are inserted beneath the artificial disc 10 during use as shown in FIG. 14.

Each tine 62 includes a thin tine body 98 with a tip 102. The tine body 98 is made thin as it is driven between the installed artificial disc 10 and the vertebra 38 during use. One outside face of the tip 102 of each tine 62 is beveled and tapers such that the distal end of the tine body 98 is thinner than the proximal tine body 98. As is visible in FIG. 4, the tine 62 is flat on the side which faces the artificial disc 10 and the tapered face of the tip 102 is located on the side of the tine body 98 which faces away from the artificial disc 10 in use. The tip 102 is shaped so that the flat inner side slides along the bone attachment surface 26, 34 of the artificial disc 10 and the tapered face of the tip 102 slides along the prepared surface of the vertebra 38; minimizing damage to the bone and wedging between the bone 38 and the artificial disc 10 to dislodge the keels 30 from the bone. Each tip 102 includes a keel tab 106 which is angled relative to the tine body 98 and which extends laterally inwardly from the tine body 98. Each keel tab 106 forms a small angular notch on the inside of each tine 62. The tine body 98 is sufficiently long to capture the artificial disc 10 in a space 112 (FIGS. 4, 17) between tines 62 in the assembled extraction tool 46 receives an artificial disc 10.

The upper arms 58 and lower arms 58 are angled slightly apart from each other in the open, insertion configuration. The upper arms 58 and lower arms 58 flex or pivot towards each other into a closed configuration which allows the extraction tool 46 to engage and capture the artificial disc keels 30. An actuator, collar 134, is disposed around the body 54 of the extraction tool 46. Parts of the extraction tool 46 which are covered by the collar 134 are shown to facilitate understanding of the structure. The collar 134 is internally threaded (indicated in dashed lines at 138) and threads 142 are formed on the body 54 of the extraction tool 46. The collar 134 may be rotated relative to the body 54 to advance the collar 134 distally or retract the collar proximally relative to the body 54. When the collar 134 is advanced distally, the distal end of the collar 134 engages the arms 58 and presses in the arms 58 inwardly towards each other. This moves the keel tabs 106 towards each other and captures the keel 30 between the tines 62 and keel tabs 106 as is shown in FIG. 16. The actuator, collar 134, may also function as a clamp which presses the upper arms 58 towards the lower arms 58 to thereby press the tines 62 against the artificial disc 10.

FIG. 17 shows a side view of the extraction tool 46. The extraction tool 46 may include an upper member 50 and a lower member 52 which may be inserted separately between the artificial disc 10 and vertebra 38.

In use, the tines 62 of the extraction tool 46 are driven between the artificial disc 10 and the vertebrae 38 to separate the artificial disc from the vertebrae 38. The collar 134 is then rotated and advanced distally along the body 54 to move the arms 58 and tines 62 towards each other and capture the artificial disc keels 30 between the tines 62 and keel tabs 106. A slap hammer 118 may be attached to the extraction tool 46 if desired and the extraction tool may be moved proximally away from the spine to remove the artificial disc 10 from between the vertebrae 38. The collar 134 may then be rotated and retracted proximally along the body 54 to release the artificial disc 10. The extraction tool 46 may include first indicator marks 146 which show how far to insert to the extraction tool 46 relative to the artificial disc 10 and second indicator marks 150 which show how far to advance the actuator/collar 134 to move the arms 58 inwardly and capture the keel 30 with the tines 62 and keel tabs 106. The extraction tool 46 may include shoulders 154 disposed between the tines 62 and arms 58 which provide a reference for insertion of the extraction tool 46 between the artificial disc 10 and vertebrae 38 and which may contact the artificial disc 10 at full insertion.

Figure 18:
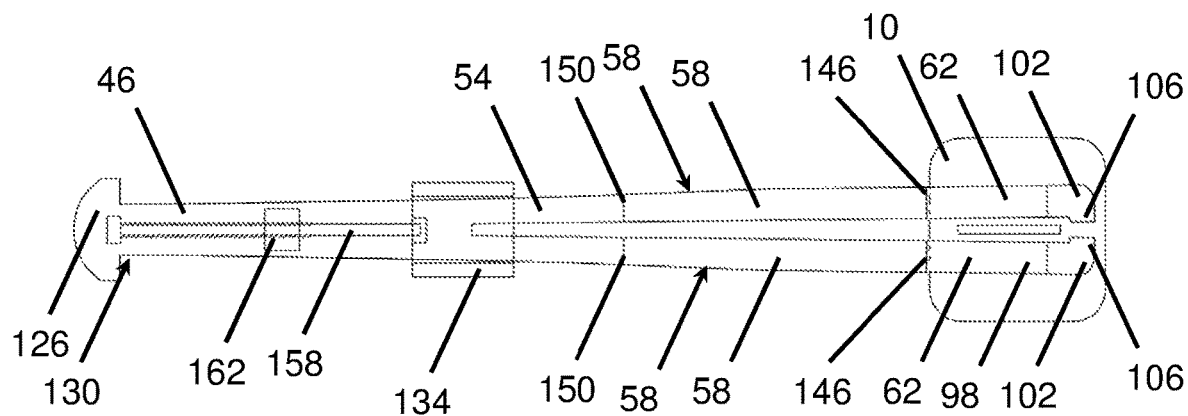
FIG. 18 is a drawing showing a top view of an artificial disc extraction tool.
Figure 19:
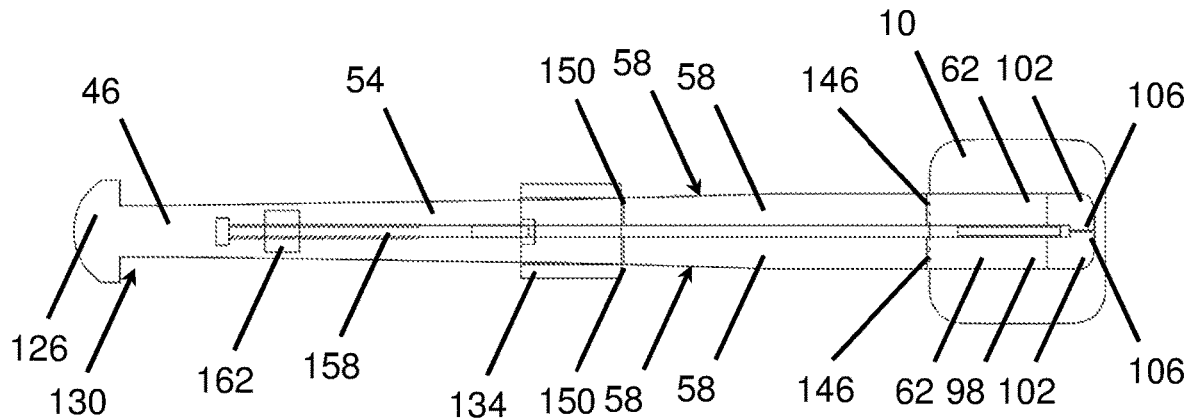
FIG. 19 is a drawing showing a top view of the artificial disc extraction tool of FIG. 18.
Figure 20:
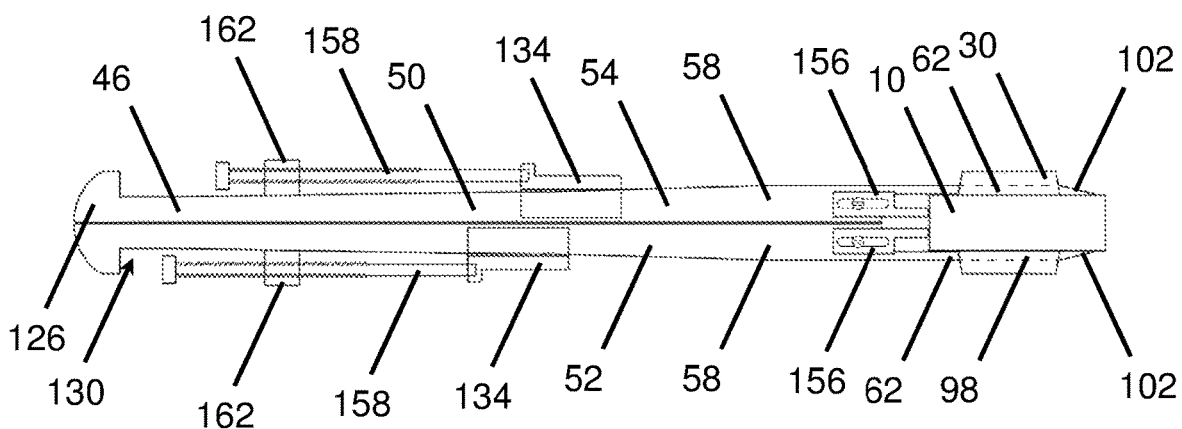
FIG. 20 is a drawing showing a side view of the artificial disc extraction tool of FIG. 18.

FIG. 18 through 20 show an extraction tool 46 configured to extract an artificial disc 10 with a single keel 30 on each of the top and bottom of the artificial disc 10. FIG. 18 shows a top view of the extraction tool 46 with the tines 62 expanded in an insertion position. FIG. 19 shows a top view of the extraction tool 46 with the tines 62 moved inwardly in a closed position where they capture the keels 30. FIG. 20 shows a side view of the extraction tool 46. The extraction tool 46 functions as discussed above and particularly in the same manner as in FIGS. 15 through 17 except that the extraction tool 46 includes a collar 134 which is positioned along the extraction tool 46 with a threaded actuator rod 158. The actuator rod 158 may have a distal end which is attached to the collar 134 and which rotates relative to the collar 134. The proximal portion of the actuator rod 158 includes threads and engages a threaded boss 162 on the extraction tool body 54. The proximal end of the actuator rod 158 includes a drive socket (such as a Torx socket) and receives a drive tool to rotate the actuator rod 158 and advance or retract the collar distally or proximally along the extraction tool body 54. FIG. 20 shows how the upper member 50 of the extraction tool and the lower member 52 of the extraction tool 46 may each have a separate collar 134, actuator rod 158, and threaded boss 162. This allows each member of the extraction tool 46 to be inserted and locked around the artificial disc keel 30 separately. FIG. 20 also shows how a fixed or adjustable depth stop 156 may be attached to an arm 58 of each extraction tool member. The depth stop 156 may contact the bone 38 or artificial disc 10 at full insertion of the extraction tool 46.

Figure 21:
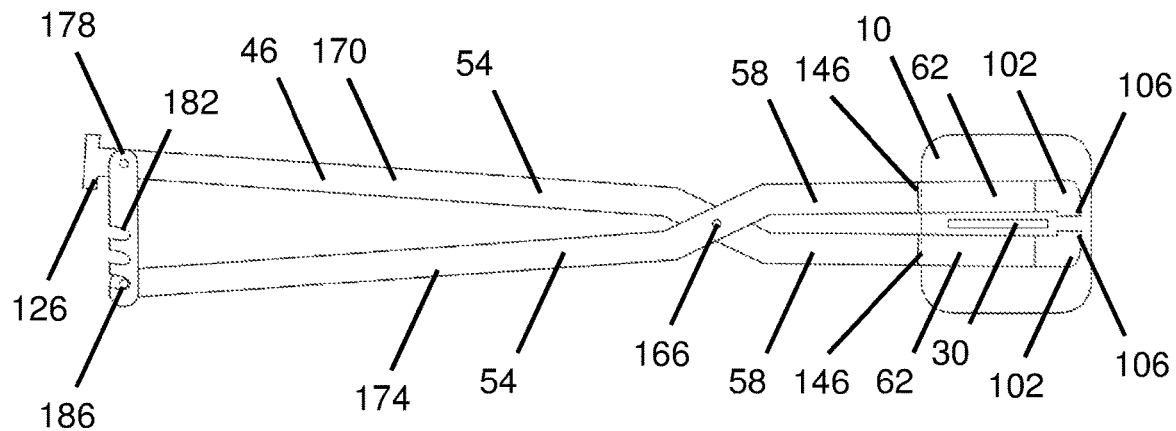
FIG. 21 is a drawing showing a top view of an artificial disc extraction tool.

FIG. 21 shows a top view of an extraction tool 46. The extraction tool 46 operates similarly to pliers and is configured to extract an artificial disc 10 with a single keel 30 on top and on bottom of the artificial disc 10. The extraction tool 46 includes upper arms 58 and lower arms 58 which are attached together at a pivot point 166 and extend distally from the extraction tool body 54. Tines 62 are disposed on the distal ends of the arms. Each tine 62 includes a thin tine body 98 with a tip 102. The tine body 98 is made thin as it is driven between the installed artificial disc 10 and the vertebra 38 during use. One outside face of the tip 102 of each tine 62 is beveled and tapers such that the distal end of the tine body 98 is thinner than the proximal tine body 98. As is visible in FIG. 4, the tine 62 is flat on the side which faces the artificial disc 10 and the tapered face of the tip 102 is located on the side of the tine body 98 which faces away from the artificial disc 10 in use. The tip 102 is shaped so that the flat inner side slides along the bone attachment surface 26, 34 of the artificial disc 10 and the tapered face of the tip 102 slides along the prepared surface of the vertebra 38; minimizing damage to the bone and wedging between the bone 38 and the artificial disc 10 to dislodge the keels 30 from the bone. Each tip 102 includes a keel tab 106 which is angled relative to the tine body 98 and which extends laterally inwardly from the tine body 98. Each keel tab 106 forms a small angular notch on the inside of each tine 62. The tine body 98 is sufficiently long to capture the artificial disc 10 in a space 112 (FIG. 4) between tines 62 in the assembled extraction tool 46 receives an artificial disc 10.

The body 54 of the extraction tool 46 includes two handles 170, 174. Each handle 170, 174 may be attached to an upper arm 58 and a lower arm 58. The handles 170, 174 may be pivoted towards each other after the tines 62 are inserted between the artificial disc 10 and the vertebrae to pivot the tines 62 towards each other and capture the keel 30 and then extract the artificial disc 10. A latch mechanism such as a locking strap 178 may be pivotably attached to one handle 170 and include notches 182, 186 to engage the other handle 174 and alternately hold the handles in an open, insertion position or a closed, extraction position. One handle 170 may include a shoulder 126 and recess 130 to allow attachment of a slap handle 118.

Figure 22:
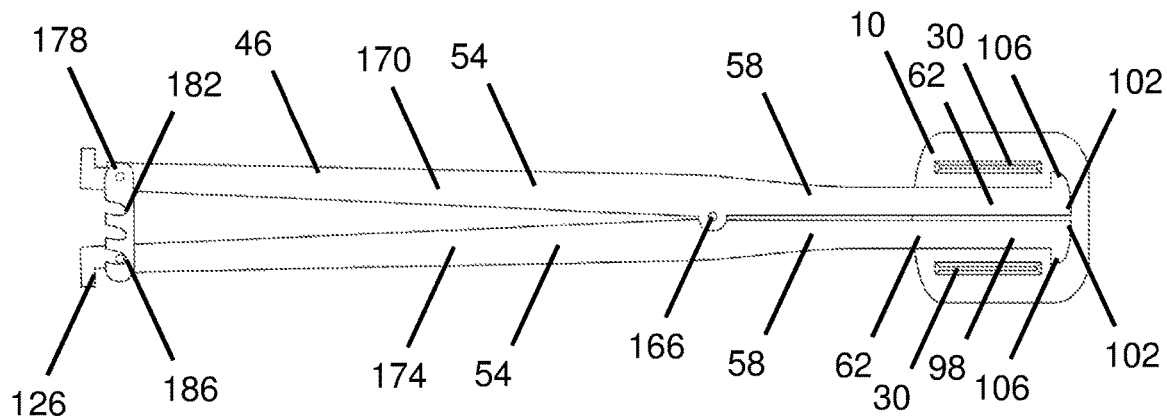
FIG. 22 is a drawing showing a top view of an artificial disc extraction tool.

FIG. 22 shows a top view of an extraction tool 46. The extraction tool 46 operates similarly to pliers and is configured to extract an artificial disc 10 with two keels 30 on top and two keels 30 on bottom of the artificial disc 10. The extraction tool 46 includes upper arms 58 and lower arms 58 which are attached together at a pivot point 166 and extend distally from the extraction tool body 54. Tines 62 are disposed on the distal ends of the arms. Each tine 62 includes a thin tine body 98 with a tip 102. The tine body 98 is made thin as it is driven between the installed artificial disc 10 and the vertebra 38 during use. One outside face of the tip 102 of each tine 62 is beveled and tapers such that the distal end of the tine body 98 is thinner than the proximal tine body 98. As is visible in FIG. 4, the tine 62 is flat on the side which faces the artificial disc 10 and the tapered face of the tip 102 is located on the side of the tine body 98 which faces away from the artificial disc 10 in use. The tip 102 is shaped so that the flat inner side slides along the bone attachment surface 26, 34 of the artificial disc 10 and the tapered face of the tip 102 slides along the prepared surface of the vertebra 38; minimizing damage to the bone and wedging between the bone 38 and the artificial disc 10 to dislodge the keels 30 from the bone. Each tip 102 includes a keel tab 106 which is angled relative to the tine body 98 and which extends laterally inwardly from the tine body 98. Each keel tab 106 forms a small angular notch on the inside of each tine 62. The tine body 98 is sufficiently long to capture the artificial disc 10 in a space 112 (FIG. 4) between tines 62 in the assembled extraction tool 46 receives an artificial disc 10.

The body 54 of the extraction tool 46 includes two handles 170, 174. Each handle 170, 174 may be attached to an upper arm 58 and a lower arm 58. The handles 170, 174 may be pivoted towards each other after the tines 62 are inserted between the artificial disc 10 and the vertebrae to pivot the tines 62 away from each other and capture the keels 30 with the keel tabs 106 and then extract the artificial disc 10. A latch mechanism such as a locking strap 178 may be pivotably attached to one handle 170 and include notches 182, 186 to engage the other handle 174 and alternately hold the handles in an open, insertion position or a closed, extraction position. One or both handles 170, 174 may include a shoulder 126 and recess 130 to allow attachment of a slap handle 118.

With the plier embodiments of the extraction tools 46 shown in FIGS. 21 and 22, a single extraction tool 46 may include upper arms 58 and lower arms 58 and engage both the top and bottom of the artificial disc 10. Alternatively, a separate extraction tool upper member 50 and lower member 52 may be provided with the shape shown in FIGS. 21 and 22. The extraction tool halves 50, 52 may be inserted separately around the artificial disc 10 and the artificial disc may then be removed.

Figure 23:
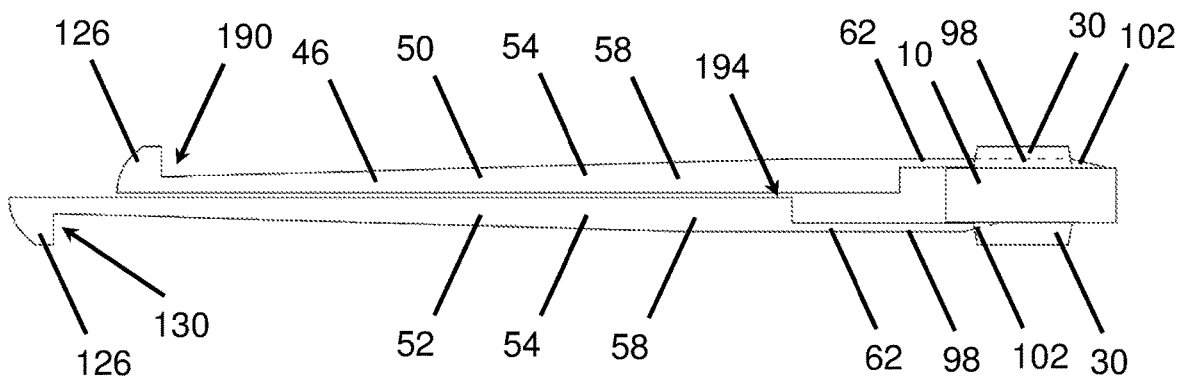
FIG. 23 is a drawing showing a side view of an artificial disc extraction tool.
Figure 24:
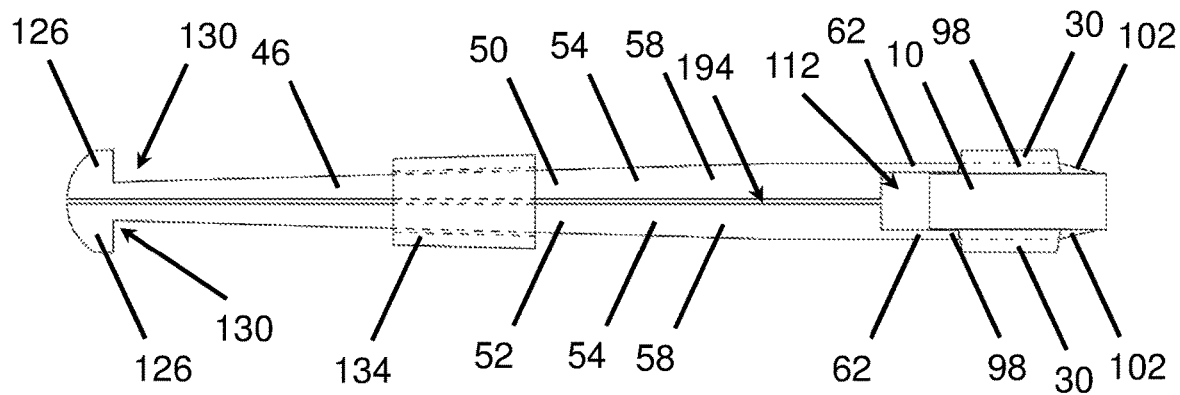
FIG. 24 is a drawing showing a side view of the artificial disc extraction tool of FIG. 23.
Figure 25:
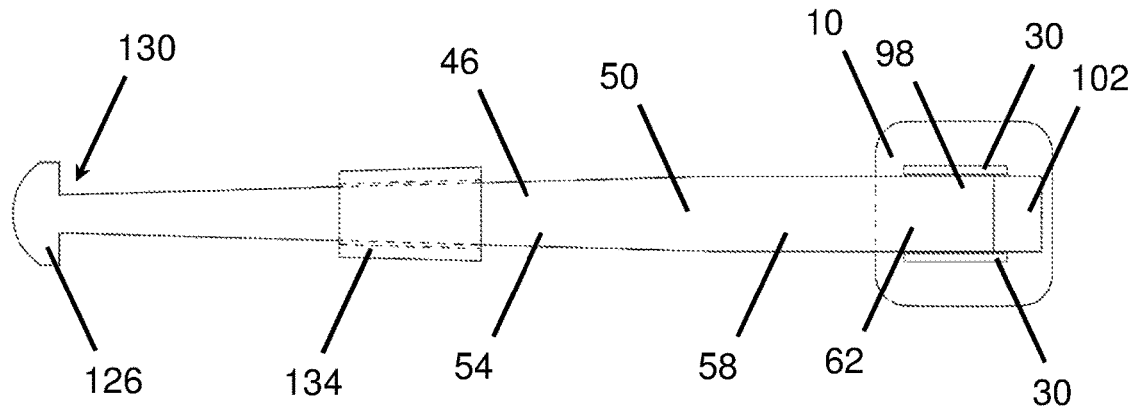
FIG. 25 is a drawing showing a top view of the artificial disc extraction tool of FIG. 23.

FIGS. 23 through 26 show an extraction tool 46 configured to extract an artificial disc 10 with two keels 30 on each on the upper bone attachment surface 26 and two keels on the lower attachment surface 34 of the artificial disc 10. FIGS. 23 and 24 show side views of the extraction tool 46. FIG. 25 shows a top view of the extraction tool 46. The extraction tool 46 functions as discussed above except as otherwise noted. The extraction tool 46 includes an upper member 50 with a body 54, an upper arm 58 which extends distally from the body 54, and a tine 62 disposed at the distal end of the arm 58. The extraction tool 46 also includes a lower member 52 with a lower arm 58 which extends distally from the body 54, and a tine 62 disposed at the distal ends of the lower arm 58. The upper member 50 of the extraction tool and the lower portion of the extraction tool are separate; allowing the upper member 50 and lower member 52 to be inserted between an artificial disc 10 and the adjacent vertebrae independently. The upper tines 62 are inserted above the artificial disc 10 and the lower tines 62 are inserted beneath the artificial disc 10 during use as shown in FIG. 14.

Each tine 62 includes a thin tine body 98 with a tip 102. The tine body 98 is made thin as it is driven between the installed artificial disc 10 and the vertebra 38 during use. One outside face of the tip 102 of each tine 62 is beveled and tapers such that the distal end of the tine body 98 is thinner than the proximal tine body 98. The tine 62 is flat on the side which faces the artificial disc 10 and the tapered face of the tip 102 is located on the side of the tine body 98 which faces away from the artificial disc 10 in use and contacts the vertebra 38. The tine 62 is shaped so that the flat inner side slides along the bone attachment surface 26, 34 of the artificial disc 10 and the tapered face of the tip 102 slides along the prepared surface of the vertebra 38; minimizing damage to the bone and wedging between the bone 38 and the artificial disc 10 to dislodge the keels 30 from the bone. The tine body 98 is sufficiently long to capture the artificial disc 10 in a space 112 between tines 62 in the assembled extraction tool 46 as the extraction tool receives an artificial disc 10.

The proximal end of the extraction tool 46 includes shoulders 126 and a recess 130 located distally from the shoulders 126. A slap handle 118 may be attached to the shoulders 126 and used to extract the artificial disc 10 if desired. The distal end of the extraction tool may be rounded to allow it to me more easily driven between the artificial disc 10 and a vertebra 38.

FIG. 24 shows the extraction tool fully inserted around an installed artificial disc 10. The tines 62 extend along the anterior/posterior length of the artificial disc 10 and both the upper member 50 and the lower member 52 of the extraction tool 46 have been inserted to an equal depth relative to the artificial disc 10. A clamp, collar 134, may be placed around the extraction tool body 54 and used to clamp the tines 62 against the artificial disc 10. The collar 134 may be a C-shaped collar which has an opening along its length and which allows it to be placed over the proximal end of the extraction tool body 54. Alternatively, the collar 134 may be larger in diameter than the proximal end of the extraction tool 46 (e.g. the shoulders 126) and the collar 134 may be placed over the proximal end of the extraction tool 46 and over the tool body 54. The extraction tool body 54 tapers and becomes larger towards the distal end such that the proximal end of the extraction tool body 54 is smaller and the distal end of the extraction tool body 54 is larger. Moving the collar 134 towards the distal end of the extraction tool 46 will cause the collar 134 to engage the extraction tool body 54 and press the upper member 50 and lower member 52 of the extraction tool 46 against each other. This will secure the artificial disc 10 between the tines 62. The extraction tool body 54 and the interior of the collar 134 may be threaded and these engaging threads may be used to advance the collar distally along the tool body 54.

The net distance 112 between the tines 62 is slightly less than the thickness of the artificial disc 10 so that a small space 194 is left between the upper member 50 and lower member 52 of the extraction tool 46. This space 194 allows the collar 134 to press the tines 62 against the artificial disc 10.

FIG. 25 shows a top view of the extraction tool 46 and the artificial disc 10. In the example embodiment, the tines 62 do not have keel tabs 106 and may simply slide between the keels 30. The tines 62 may be made wider than the spacing between the keels 30 and one or more slots may be formed in the tines 62 which each allow a keel 30 to enter into a slot as the tines 62 are inserted around the artificial disc 10. This may allow a similarly designed extraction tool to function with an artificial disc 10 with a single keel 30 or with other numbers of keels 30. In many instances, there is little resistance to removing the artificial disc 10 once the tines 62 have been inserted between the bone attachment surfaces 26, 34 and the vertebrae 38. In these situations, the artificial disc 10 may be removed with just the frictional grip between the tines 62 and the bone attachment surfaces 26, 34.

Figure 26:
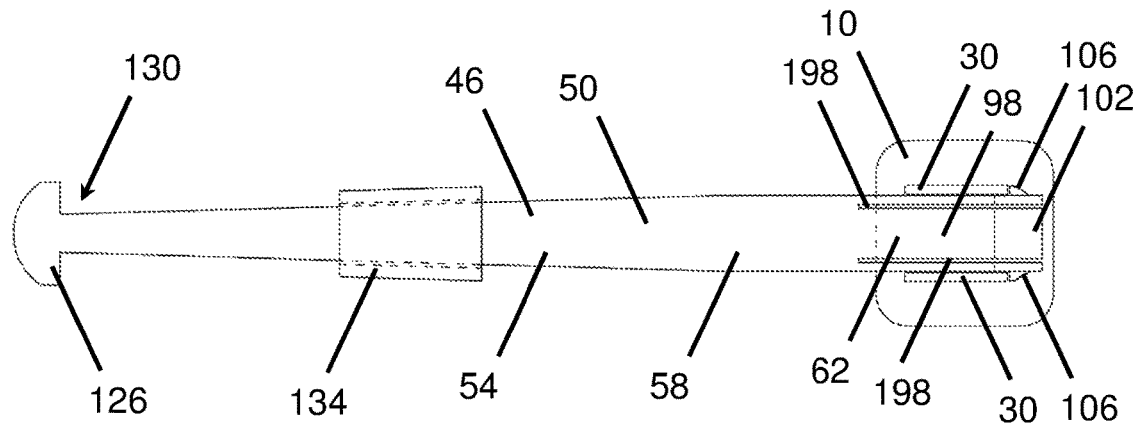
FIG. 26 is a drawing showing a top view of the artificial disc extraction tool of FIG. 23.

The extraction tool 46 may alternatively have small keel tabs 106 which are spring loaded and extend from the tines 62 once the tines 62 are inserted past the keels. The tines 62 may also have longitudinal slots 198 therethrough with increase their lateral flexibility and small keel tabs 106 as shown in FIG. 26. The slots 198 create smaller fingers in the tines 62 which flex inwardly during insertion and allow the keel tabs 106 to pass between the keels 30 and then spring back outwardly once the tine 62 is fully inserted along the artificial disc 10.

Figure 27:
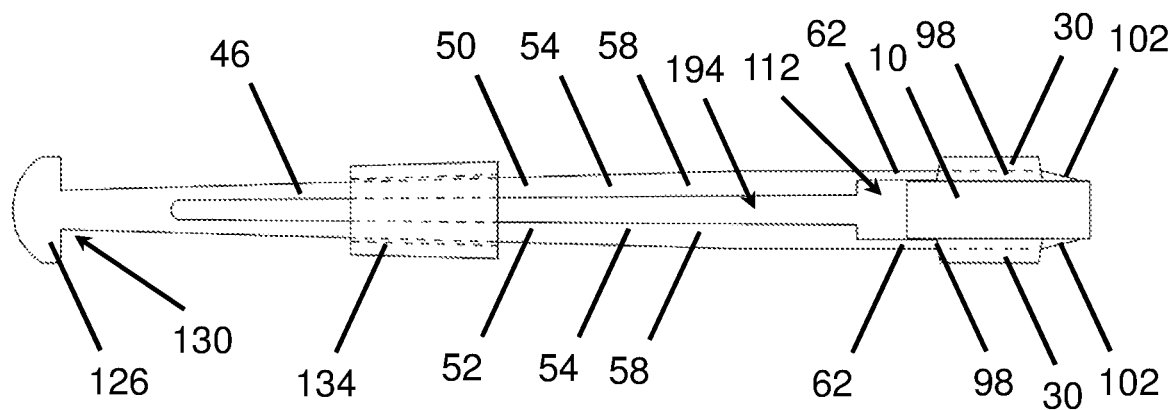
FIG. 27 is a drawing showing a side view of an artificial disc extraction tool.
Figure 28:
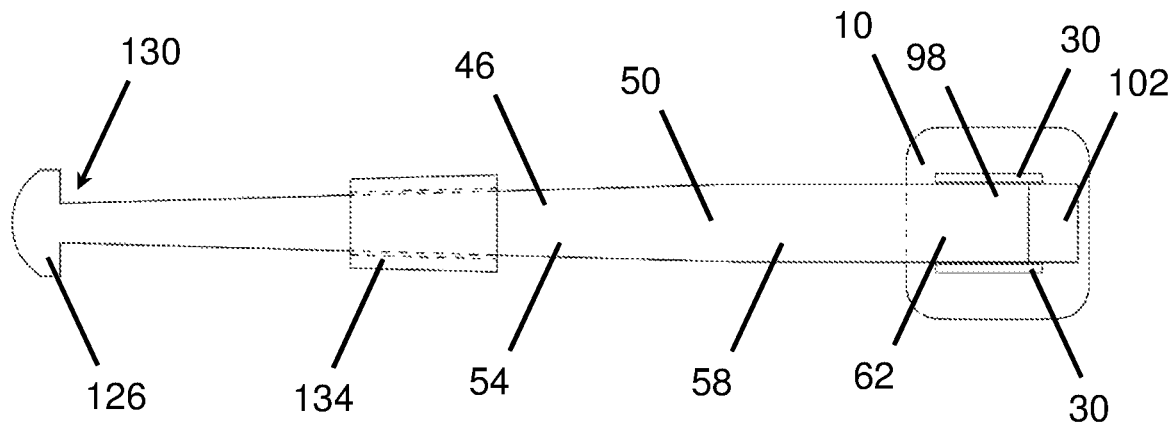
FIG. 28 is a drawing showing a top view of the artificial disc extraction tool of FIG. 27.
Figure 29:
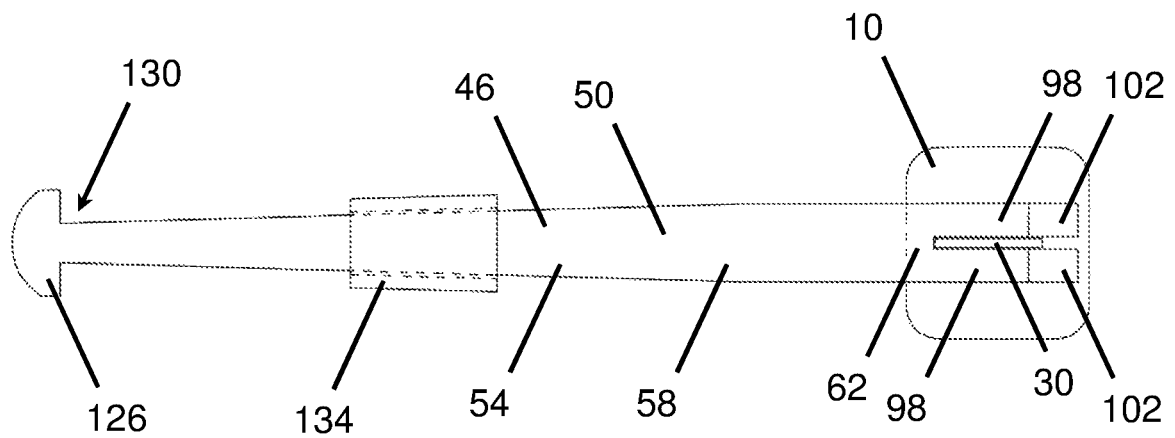
FIG. 29 is a drawing showing a top view of the artificial disc extraction tool of FIG. 27.

FIGS. 27 through 29 show another extraction tool 46 configured to extract an artificial disc 10 with two keels 30 on each on the upper bone attachment surface 26 and two keels on the lower attachment surface 34 of the artificial disc 10. FIG. 27 shows a side view of the extraction tool 46. FIG. 28 shows a top view of the extraction tool 46. The extraction tool 46 functions as discussed above except as otherwise noted. The upper member 50 and lower member 52 of the extraction tool 46 are joined together at the proximal end of the extraction tool 46. The upper arm 58 and a lower arm 58 extend distally from the body 54. A tine 62 is disposed at the distal end of each of the upper arm 58 and lower arm 58. The upper member 50 of the extraction tool and the lower member 52 of the extraction tool are joined together at the proximal end of the extraction tool 46, allowing the upper member 50 and lower member 52 to be inserted together between the respective upper bone attachment surface 26 and lower bone attachment surface 34 of an artificial disc 10 and the adjacent vertebrae 38 at the same time. The upper tine 62 is inserted above the artificial disc 10 and the lower tine 62 is inserted beneath the artificial disc 10 during use as shown in FIG. 14.

Each tine 62 includes a thin tine body 98 with a tip 102. The tine body 98 is made thin as it is driven between the installed artificial disc 10 and the vertebra 38 during use. One outside face of the tip 102 of each tine 62 is beveled and tapers such that the distal end of the tine body 98 is thinner than the proximal tine body 98. The tine 62 is flat on the side which faces the artificial disc 10 and the tapered face of the tip 102 is located on the side of the tine body 98 which faces away from the artificial disc 10 in use and contacts the vertebra 38. The tine 62 is shaped so that the flat inner side slides along the bone attachment surface 26, 34 of the artificial disc 10 and the tapered face of the tip 102 slides along the prepared surface of the vertebra 38; minimizing damage to the bone and wedging between the bone 38 and the artificial disc 10 to dislodge the keels 30 from the bone. The tine body 98 is sufficiently long to capture the artificial disc 10 in a space 112 between tines 62 in the assembled extraction tool 46 as the extraction tool receives an artificial disc 10.

The proximal end of the extraction tool 46 includes shoulders 126 and a recess 130 located distally from the shoulders 126. A slap handle 118 may be attached to the shoulders 126 and used to extract the artificial disc 10 if desired. The distal end of the extraction tool may be rounded to allow it to me more easily driven between the artificial disc 10 and a vertebra 38.

The extraction tool is shown fully inserted around an installed artificial disc 10. The tines 62 extend along the anterior/posterior length of the artificial disc 10 and both the upper member 50 and the lower member 52 of the extraction tool 46 have been inserted to an equal depth relative to the artificial disc 10. A clamp, collar 134, disposed around the extraction tool body 54 may be used to clamp the tines 62 against the artificial disc 10. The extraction tool body 54 tapers and becomes larger towards the distal end such that the proximal end of the extraction tool body 54 is smaller and the distal end of the extraction tool body 54 is larger. Moving the collar 134 towards the distal end of the extraction tool 46 will cause the collar 134 to engage the extraction tool body 54 and press the upper member 50 and lower member 52 of the extraction tool 46 against each other. This will secure the artificial disc 10 between the tines 62. The extraction tool body 54 and the inside surface of the collar 134 may be smooth and the collar 134 may be slid distally along the extraction tool body 54. Alternatively, the extraction tool body 54 and the interior of the collar 134 may be threaded as shown previously and these engaging threads may be used to advance the collar distally along the extraction tool body 54.

The net distance 112 between the tines 62 (e.g. the distance with the upper member 50 and lower member 52 of the extraction tool fully compressed together) is slightly less than the thickness of the artificial disc 10 so that a small space 194 is left between the upper member 50 and lower member 52 of the extraction tool 46. This space 194 allows the collar 134 to press the tines 62 against the artificial disc 10.

FIG. 28 shows a top view of the extraction tool 46 and the artificial disc 10. In the example embodiment, the tines 62 do not have keel tabs 106 and may simply slide between the keels 30. The tines 62 may be made wider than the spacing between the keels 30 and one or more slots may be formed in the tines 62 which each allow a keel 30 to enter into a slot as the tines 62 are inserted around the artificial disc 10. This may allow a similarly designed extraction tool to function with an artificial disc 10 with a single keel 30 or with other numbers of keels 30. In many instances, there is little resistance to removing the artificial disc 10 once the tines 62 have been inserted between the bone attachment surfaces 26, 34 and the vertebrae 38. In these situations, the artificial disc 10 may be removed with just the frictional grip between the tines 62 and the bone attachment surfaces 26, 34.

The extraction tool 46 may alternatively have small keel tabs 106 which are spring loaded and extend from the tines 62 once the tines 62 are inserted past the keels. The tines 62 may also have longitudinal slots 198 therethrough with increase their lateral flexibility and small keel tabs 106 as shown in FIG. 26. The slots 198 create smaller fingers in the tines 62 which flex inwardly during insertion and allow the keel tabs 106 to pass between the keels 30 and then spring back outwardly once the tine 62 is fully inserted along the artificial disc 10.

Figure 30:
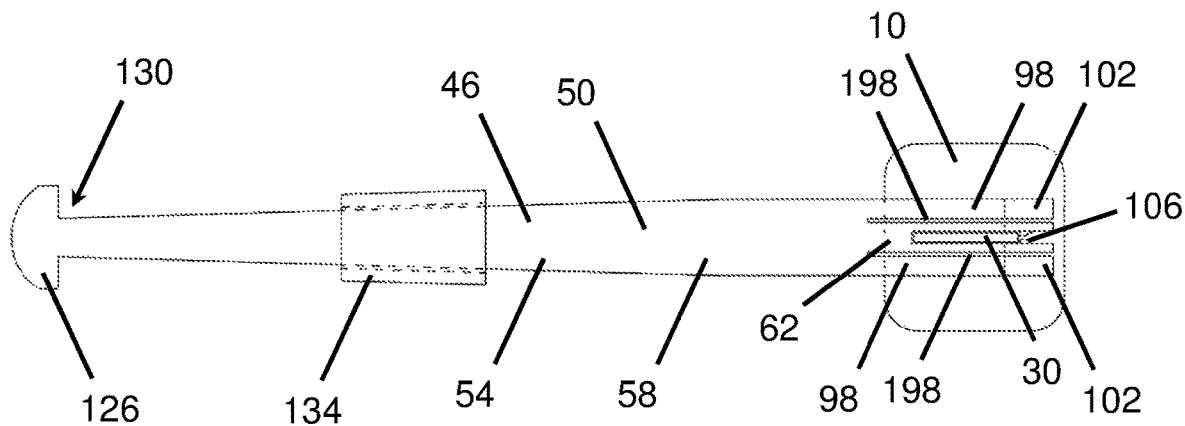
FIG. 30 is a drawing showing a top view of the artificial disc extraction tool of FIGS. 23 and 27.

FIG. 29 shows a top view of the extraction tool 46 of FIGS. 23 through 26 or of the extraction tool 46 of FIGS. 27 and 28. This drawing illustrates how the extraction tool tines 62 may be modified to include a slot 202 which receives a keel 30, such as in the artificial disc 10 which includes a single keel 30 on the upper bone attachment surface 26 and the lower bone attachment surface 34. FIG. 30 similarly shows a top view of the extraction tool 46 of FIGS. 23 through 26 or of the extraction tool 46 of FIGS. 27 and 28 and illustrates how the (upper and lower) tines 62 may be modified to include keel tabs 106. The keel tabs 106 engage the keel 30 once the extraction tool 46 is inserted completely relative to the artificial disc 10. The tines 62 may also have longitudinal slots 198 therethrough which increase the lateral flexibility and small keel tabs 106 as shown in FIG. 26. The slots 198 create smaller fingers in the tines 62 which flex inwardly during insertion and allow the keel tabs 106 to pass between the keels 30 and then spring back outwardly once the tine 62 is fully inserted along the artificial disc 10.

Figure 31:
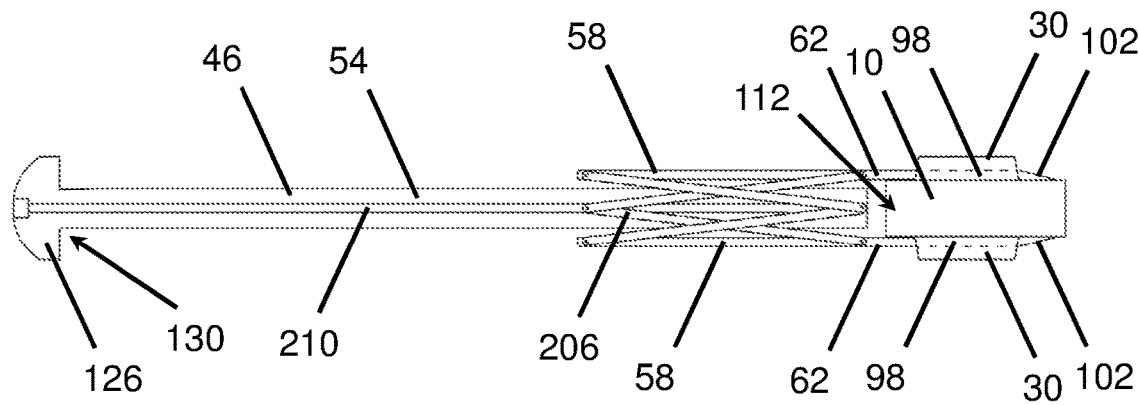
FIG. 31 is a drawing showing a side view of an artificial disc extraction tool.

FIG. 31 shows a side view of another extraction tool 46. The extraction tool 46 is as described above and functions in the above manner except as noted. An upper arm 58 and a lower arm 58 are attached to the body 54 by a scissor mechanism 206. A tine 62 is disposed at the distal end of each of the upper arm 58 and lower arm 58. The scissor mechanism 206 is movable via a central drive rod 210 to move the upper member 50 of the extraction tool 46 and the lower member 52 of the extraction tool 46 farther apart or closer together. The drive rod 210 may be a threaded rod which interacts with a threaded hole in the proximal center link of the scissor mechanism 206. The scissor mechanism 206 may be used to adjust the spacing 112 between the tines 62 to accommodate different thickness of artificial discs 10 and also to press the tines 62 against the artificial disc bone attachment surfaces 26, 34.

The upper tine 62 and lower tine 62 are inserted together between the respective upper bone attachment surface 26 and lower bone attachment surface 34 of an artificial disc 10 and the adjacent vertebrae 38 at the same time. The upper tine 62 is inserted above the artificial disc 10 and the lower tine 62 is inserted beneath the artificial disc 10 during use as shown in FIG. 14. Each tine 62 includes a thin tine body 98 with a tip 102. The tine body 98 is made thin as it is driven between the installed artificial disc 10 and the vertebra 38 during use. One outside face of the tip 102 of each tine 62 is beveled and tapers such that the distal end of the tine body 98 is thinner than the proximal tine body 98. The tine 62 is flat on the side which faces the artificial disc 10 and the tapered face of the tip 102 is located on the side of the tine body 98 which faces away from the artificial disc 10 in use and contacts the vertebra 38. The tine 62 is shaped so that the flat inner side slides along the bone attachment surface 26, 34 of the artificial disc 10 and the tapered face of the tip 102 slides along the prepared surface of the vertebra 38; minimizing damage to the bone and wedging between the bone 38 and the artificial disc 10 to dislodge the keels 30 from the bone. The tine body 98 is sufficiently long to capture the artificial disc 10 in a space 112 between tines 62 in the assembled extraction tool 46 as the extraction tool receives an artificial disc 10. The tines 62 may typically be as shown and described with respect to FIGS. 23 through 30.

The proximal end of the extraction tool 46 includes shoulders 126 and a recess 130 located distally from the shoulders 126. A slap handle 118 may be attached to the shoulders 126 and used to extract the artificial disc 10 if desired. The distal end of the extraction tool may be rounded to allow it to me more easily driven between the artificial disc 10 and a vertebra 38.

Figure 32:
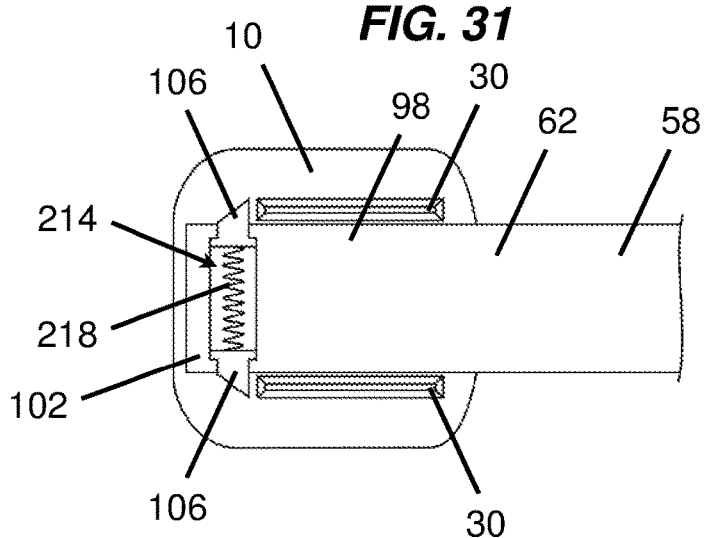
FIG. 32 is a drawing showing a top view of the tines of an artificial disc extraction tool.

FIG. 32 shows a detailed drawing of a tine 62 on an extraction tool 46. The tine 62 includes keel tabs 106 which may retract within a channel or pocket 214 in the tine 62. A spring 218 is disposed between the keel tabs 106 in the pocket 214. The spring 218 presses the keel tabs 106 out of the pocket 214 as shown. Shoulders formed in the ends of the pocket 214 and on the ends of the keel tabs 106 keep the keel tabs retained within the pocket 214. The keel tabs are beveled on their distal faces and are pushed inwardly into the pocket 214 as the tine 62 is pushed between two keels. Once the tine 62 is moved sufficiently past the keels 30, the keel tabs 106 extend outwardly from the pocket 214 and engage the keel 30 when the tine 62 is pulled proximally to extract the artificial disc 10. The spring loaded keel tabs 106 may also be used on a single keel design by having a slot through the center of the tine 62 to receive the keel 30 between two portions of the tine 62, pockets 214 formed on both sides of the slot, springs 218 in each pocket 214, and keel tabs 106 which are biased inwardly to the slot by the springs.

Referring to all of the above extraction tools 46; artificial discs 10 may commonly be between about 0.5 cm thick and about 1.5 cm thick, between about 1 cm long and about 4 cm long, and between about 1 cm wide and about 4 cm wide. These dimensions vary with the location of the artificial disc 10 in the spine and the size of the patient. Accordingly, the extraction tool 46 is dimensioned to receive such an artificial disc 10. Commonly, the extraction tool 46 is between about 10 cm long and about 20 cm long. The extraction tool vertebral space 112 (the space between the tines 62) is often between about 0.5 cm and 1.5 cm and the tines 62 are often between about 1 cm and about 5 cm long to receive the desired artificial disc 10. The tines 62 are often between about 0.5 mm and 2 mm thick and between about 5 mm wide and about 20 mm wide. The tines 62 are wider than they are thick, and often have a width which is about 5 times, about 10 times, or about 15 times their thickness. Commonly, the tines 62 have a width which is between about 5 times and about 15 times their thickness, or a width which is between about 5 times and about 10 times their thickness. The tapered tip 102 of the tines 62 is often between about 0.5 cm and about 1.5 cm long and the distal tip of the tines 62 is often between about 0.1 mm and about 0.5 mm thick. The tines 62 are parallel to each other and generally planar. The tines 62 are disposed in parallel horizontal planes (relative to an upright extraction tool 46 or an upright artificial disc 10) with a vertical space between the tines to receive an artificial disc 10. The upper tine 62 has a lower surface which is an artificial disc engaging surface that is placed adjacent the upper bone attachment surface of the artificial disc and grips the upper bone attachment surface to remove the artificial disc form a spine. The upper tine 62 has an upper surface which is a vertebra releasing surface which releases or separates an upper vertebra from the artificial disc upper bone attachment surface. The lower tine 62 has an upper surface which is an artificial disc engaging surface that is placed adjacent the lower bone attachment surface of the artificial disc and grips the lower attachment surface to remove the artificial disc from a spine. The lower tine 62 has a lower surface which is a vertebra releasing surface which releases or separates a lower vertebra from the artificial disc lower bone attachment surface. In use, the upper tine upper bone releasing surface separates an artificial disc from an upper vertebra and the lower tine lower bone releasing surface separates the artificial disc from a lower vertebra. The upper tine lower artificial disc engaging surface grips the upper surface of the artificial disc and the lower tine upper artificial disc engaging surface grips the lower surface of the artificial disc and the extraction tool removes the artificial disc from the spine.

The extraction tool 46 separates the artificial disc 10 from the vertebrae 38 with minimal damage to the vertebral bone and minimal trauma to the surrounding tissue and allows for easier removal of the artificial disc 10. This allows the prepared surface of the vertebra to be reused for implanting an artificial disc 10 without further resection in many instances, reducing surgical complications.

The above description of illustrated examples of the present invention, including what is described in the Abstract, is not intended to be exhaustive or to be limitation to the precise forms disclosed. While specific examples of the invention are described herein for illustrative purposes, various equivalent modifications are possible without departing from the broader scope of the present claims. Indeed, it is appreciated that specific example dimensions, materials, etc., are provided for explanation purposes and that other values may also be employed in other examples in accordance with the teachings of the present invention.

What is claimed is:
1. An artificial spinal disc extraction tool for removing an installed artificial spinal disc from between vertebrae comprising:
    an upper member having an upper body;
    a first upper arm extending distally from the upper body;
    a first upper tine extending distally from a distal end of the first upper arm wherein a distal end of the first upper tine comprises a first keel tab which extends laterally from the distal end of the first upper tine;
    a second upper arm extending distally from the upper body;
    a second upper tine extending distally from a distal end of the second upper arm wherein a distal end of the second upper tine comprises a second keel tab which extends laterally from the distal end of the second upper tine;
    an upper actuator which engages the first upper arm and the second upper arm and moves the first upper arm laterally relative to the second upper arm to thereby change a distance between the first upper tine and the second upper tine;
    a lower member having a lower body;
    a first lower arm extending distally from the lower body;
    a first lower tine extending distally from a distal end of the first lower arm;
    a second lower arm extending distally from the lower body;

a second lower tine extending distally from a distal end of the second lower arm; and a lower actuator which engages the first lower arm and the second lower arm and moves the first lower arm laterally relative to the second lower arm to thereby change a distance between the first lower tine and the second lower tine.

2. The extraction tool of claim 1, wherein the extraction tool is used by inserting the first upper tine and the second upper tine between an artificial disc upper bone attachment surface and an attached upper vertebra such that the first upper tine and the second upper tine separate the artificial disc from the upper vertebra and by inserting the first lower tine and the second lower tine between an artificial disc lower bone attachment surface and an attached lower vertebra such that the first lower tine and the second lower tine separate the artificial disc from the lower vertebra.

3. The extraction tool of claim 1, wherein the upper actuator extends between the first upper arm and the second upper arm and wherein moving the upper actuator longitudinally along the extraction tool causes the actuator to engage the first upper arm and the second upper arm to thereby change the distance between the first upper arm and the second upper arm.

4. The extraction tool of claim 1, wherein the extraction tool is used by inserting the first upper tine and the second upper tine between a first artificial disc upper keel and a second artificial disc upper keel, and moving the upper actuator such that the upper actuator moves the first upper tine apart from the second upper tine such that the first upper tine engages the first artificial disc upper keel and such that the second upper tine engages the second artificial disc upper keel.

5. The extraction tool of claim 4, wherein the first upper keel tab extends laterally from an outside edge of the first upper tine adjacent a tip of the first upper tine, and wherein the second upper keel tab extends laterally from an outside edge of the second upper tine adjacent a tip of the second upper tine, wherein the first upper keel tab is positioned in alignment with the first upper keel and the second upper keel tab is positioned in alignment with the second upper keel when the first upper tine is moved apart from the second upper tine.

6. The extraction tool of claim 5 wherein, during use of the extraction tool, moving the first upper tine apart from the second upper tine moves the first upper keel tab behind the first upper keel and moves the second upper keel tab behind the second upper keel.

7. The extraction tool of claim 1, wherein a distal end of the first upper tine comprises a tip which tapers in thickness and is thinner than a proximal end of the first upper tine, and wherein a distal end of the second upper tine comprises a tip which tapers in thickness and is thinner than a proximal end of the second upper tine.

8. An artificial spinal disc extraction tool for removing an installed artificial spinal disc from between vertebrae comprising:

an upper member having an upper body;
a first upper arm extending distally from the upper body;
a first upper tine extending distally from a distal end of the first upper arm, wherein the first upper tine comprises a tip portion which tapers in thickness such that the distal end of the first upper tine is thinner than a proximal portion of the first upper tine and wherein the first upper tine comprises a first upper keel tab which extends laterally from the distal end of the first upper tine;

a lower member having a lower body;
a first lower arm extending distally from the lower body;
a first lower tine extending distally from a distal end of the first lower arm, wherein the first lower tine comprises a tip portion which tapers in thickness such that the distal end of the first lower tine is thinner than a proximal portion of the first upper tine and wherein the first lower tine comprises a first lower keel tab which extends laterally from the distal end of the first lower tine; and and;

wherein the extraction tool is used by inserting the first upper tine between an artificial disc upper bone attachment surface and an attached vertebra and by inserting the first lower tine between an artificial disc lower bone attachment surface and an attached vertebra wherein the first upper keel tab is positioned behind an artificial disc upper keel and the first lower keel tab is positioned behind an artificial disc lower keel to thereby engage the artificial disc to remove the artificial disc from a vertebrae.

9. The extraction tool of claim 8, wherein the upper member comprises a second upper tine, and wherein the extraction tool comprises an upper actuator which is selectively movable to thereby move the first upper tine towards and apart from the second upper tine to allow the first upper tine and second upper tine to engage an artificial disk upper keel.

10. An artificial spinal disc extraction tool for removing an installed artificial spinal disc from between vertebrae comprising:

an upper member comprising;
an elongate body having a proximal end and a distal end;
a first upper arm which is attached to the distal end of the body and which extends distally from the distal end of the body;
a first upper tine which is attached to the distal end of the first upper arm and which extends distally from the first upper arm, the first upper tine comprising an upper bone contacting surface and a lower artificial disc contacting surface;
wherein a tip portion of the first upper tine tapers in thickness such that a distal end of the first upper tine has a thickness which is less than a thickness of the first upper tine;
a lower member comprising;
an elongate body having a proximal end and a distal end;
a first lower arm which is attached to the distal end of the body and which extends distally from the distal end of the body;
a first lower tine which is attached to the distal end of the first lower arm and which extends distally from the first lower arm, the first lower tine comprising an upper artificial disc contacting surface and a lower bone contacting surface;
wherein a tip portion of the first lower tine tapers in thickness such that a distal end of the first lower tine has a thickness which is less than a thickness of the first lower tine; and
wherein, in use, the first upper tine is inserted between an artificial disc upper bone attachment surface and an upper vertebra such that the upper bone contacting surface contacts a lower surface of the upper vertebra and the lower artificial disc contacting surface contacts an upper surface of the artificial disc and wherein the first upper tine separates the artificial disc from the upper vertebra and wherein the first lower tine is inserted between an artificial disc lower bone attachment surface and a lower vertebra such that the upper artificial disc contacting surface contacts an upper surface of the artificial disc and the lower bone contacting surface contacts an upper surface of the lower vertebra and wherein the first lower tine separates the artificial disc from the lower vertebra and wherein the extraction tool is configured to remove the artificial disc from the vertebrae.

11. The extraction tool of claim 10, wherein the upper member comprises:
   a second upper arm which is attached to the distal end of the body and which extends distally from the distal end of the body, and which is disposed adjacent the first upper arm;
   a second upper tine which is attached to the distal end of the second upper arm and which extends distally from the second upper arm;
      wherein a tip portion of the second upper tine tapers in thickness such that a distal end of the second upper tine has a thickness which is less than a thickness of the second upper tine;
   wherein the lower member comprises:
      a second lower arm which is attached to the distal end of the body and which extends distally from the distal end of the body, and which is disposed adjacent the first lower arm;
      a second lower tine which is attached to the distal end of the second lower arm and which extends distally from the second lower arm; and
         wherein a tip portion of the second lower tine tapers in thickness such that a distal end of the second lower tine has a thickness which is less than a thickness of the second lower tine; and
   wherein, in use, the second upper tine is inserted between an artificial disc upper bone attachment surface and a vertebra and the second lower tine is inserted between an artificial disc lower bone attachment surface and a vertebra.

12. The extraction tool of claim 11, wherein the first upper tine and second upper tine are movable laterally to selectively increase or decrease a distance therebetween and thereby selectively grip an artificial disc upper keel with the first upper tine and the second upper tine, and wherein the first lower tine and second lower tine are movable laterally to selectively increase or decrease a distance therebetween and thereby selectively grip an artificial disc lower keel with the first lower tine and the second lower tine.

13. The extraction tool of claim 12, further comprising a first upper keel tab extending laterally from the first upper tine and a second upper keel tab extending laterally from the second upper tine, and wherein the first upper tine and first lower tine are movable laterally to position the first upper keel tab adjacent a distal end of an artificial disc keel and to position the second upper keel tab adjacent a distal end of an artificial disc keel and thereby grip the artificial disc.

14. The extraction tool of claim 13, wherein the first upper keel tab is located on an outside side of the first upper tine, wherein the second upper keel tab is located on an outside side of the second upper tine, and wherein the first upper tine and the second upper tine are movable laterally to increase a distance between the first upper tine and second upper tine and thereby engage a first keel and a second keel with the first upper keel tab and the second upper keel tab.

15. The extraction tool of claim 12, further comprising an actuator which is movable proximally and distally relative to the upper member body and wherein movement of the actuator distally relative to the body causes the actuator to engage the first upper arm and second upper arm to thereby increase the distance between the first upper tine and the second upper tine.

16. The extraction tool of claim 15, wherein the actuator comprises an expansion pin having a threaded section, and wherein the expansion pin is rotated to move the expansion pin proximally and distally relative to the body.

17. The extraction tool of claim 16, wherein a distal end of the expansion pin engages an angled ramp on the first upper arm and thereby moves the first upper arm away from the second upper arm.

18. The extraction tool of claim 10, wherein the upper member and the lower member are joined together near a proximal end of the extraction tool, and wherein the upper member is forced towards the lower member to hold an artificial disc between the first upper tine and the first lower tine.

19. The extraction tool of claim 10, wherein the first upper tine has a thickness which is about 1 mm and a width which is between about 5 mm and about 15 mm, and wherein the first lower tine has a thickness which is about 1 mm and a width which is between about 5 mm and about 15 mm.

20. An artificial spinal disc extraction tool for removing an installed artificial spinal disc from between vertebrae comprising:
   a first member having a body;
   a first arm extending distally from the body;
   a first tine extending distally from a distal end of the first arm;
   a first keel tab extending laterally from a distal end of the first tine;
   a second arm extending distally from the body;
   a second tine extending distally from a distal end of the second arm;
   an actuator which is selectively movable to thereby move the first tine laterally towards and away from the second tine;
   wherein, during use of the extraction tool, the first tine is movable laterally relative to the second tine wherein the lateral movement of the first arm positions the first keel tab adjacent a distal end of an artificial disc keel to thereby engage an artificial disc keel and thereby grasp the artificial disc.

21. The extraction tool of claim 20, wherein the first tine and second tine are flat, elongate, and coplanar.

22. The extraction tool of claim 20, wherein the actuator is movable distally to thereby contact the first arm and the second arm and move the first arm laterally apart from the second arm.

23. The extraction tool of claim 20, wherein the actuator is positioned between the first arm and the second arm.

24. The extraction tool of claim 20, wherein the actuator comprises a pin with a threaded section, wherein the threaded section engages a complementary threaded section of the body such that rotation of the actuator moves the actuator distally relative to the body.

25. The extraction tool of claim 20, wherein the actuator comprises a tapered section and wherein movement of the actuator relative to the first arm causes the tapered section to engage an angled ramp on the first arm and thereby move the first arm laterally relative to the second arm.

26. The extraction tool of claim 20, wherein the first tine comprises a proximal body portion with a width which is greater than a thickness and a tip portion which tapers in thickness such that a distal end of the tip is thinner than a distal end of the proximal body and wherein the second tine comprises a proximal body portion with a width which is greater than a thickness and a tip portion which tapers in thickness such that a distal end of the tip is thinner than a distal end of the proximal body.

27. An artificial spinal disc extraction tool for removing an installed artificial spinal disc from between vertebrae comprising:

an upper member having a body;
a first upper tine extending distally from the upper member body, the first upper tine having an upper bone contacting surface, a lower artificial disc contacting surface disposed opposite the upper bone contacting surface, a thickness between the upper bone contacting surface and the lower artificial disc contacting surface, a width which is greater than the thickness, and a length which is greater than the thickness;
a lower member having a body;
a first lower tine extending distally from the lower member body, the first lower tine having an upper artificial disc contacting surface disposed parallel to the upper tine lower bone contacting surface wherein the upper disc contacting surface and the lower disc contacting surface are disposed inwardly between the upper tine and lower tine, a lower bone contacting surface disposed opposite the upper disc contacting surface, a thickness between the upper artificial disc contacting surface and the lower bone contacting surface, a width which is greater than the thickness, and a length which is greater than the thickness, wherein the upper bone contacting surface and the lower bone contacting surface are disposed outwardly on the upper tine and lower tine; and
wherein the upper tine and lower tine are sized and configured so that, in use, the first upper tine is suitable for insertion between an artificial disc upper bone attachment surface and an upper vertebra such that the upper bone contacting surface contacts a lower surface of the upper vertebra and the lower artificial disc contacting surface contacts an upper surface of the artificial disc and wherein the first upper tine separates the artificial disc from the upper vertebra, and wherein the first lower tine is suitable for insertion between an artificial disc lower bone attachment surface and a lower vertebra such that the upper artificial disc contacting surface contacts an upper surface of the artificial disc and the lower bone contacting surface contacts an upper surface of the lower vertebra and wherein the first lower tine separates the artificial disc from the lower vertebra.

28. The extraction tool of claim 27, wherein the first upper tine comprises a first keel tab extending laterally from a distal end of the first tine and wherein, during use of the extraction tool, lateral movement of the first tine positions the first keel tab adjacent a distal end of an artificial disc keel.

29. The extraction tool of claim 28, further comprising a second upper tine which extends adjacent the first upper tine, an actuator which is selectively movable to thereby move the first upper tine laterally towards and away from the second upper tine, and wherein, during use of the extraction tool, the first upper tine is movable laterally relative to the second upper tine wherein the lateral movement of the first upper arm positions the first keel tab adjacent a distal end of an artificial disc keel to thereby engage the artificial disc keel and apply a pulling force to the artificial disc keel.

30. The extraction tool of claim 27, wherein the first upper tine comprises a proximal body portion and a tip portion which tapers in thickness such that a distal end of the tip is thinner than a distal end of the proximal body and wherein the first lower tine comprises a proximal body portion and a tip portion which tapers in thickness such that a distal end of the tip is thinner than a distal end of the proximal body.

\* \* \* \* \*